(12) United States Patent
Marliere et al.

(10) Patent No.: US 9,102,952 B2
(45) Date of Patent: Aug. 11, 2015

(54) PROCESS FOR THE PRODUCTION OF ISOPRENOL FROM MEVALONATE EMPLOYING A DIPHOSPHO-MEVOLONATE DECARBOXYLASE

(75) Inventors: Philippe Marliere, Mouscron (BE); Maria Anissimova, Nozay (FR); Romain Chayot, Paris (FR); Marc Delcourt, Paris (FR)

(73) Assignees: Global Bioenergies SA, Evry (FR); Scientist of Fortune, Luxembourg (LU)

( * ) Notice: Subject to any disclaimer, the term of this patent is extended or adjusted under 35 U.S.C. 154(b) by 0 days.

(21) Appl. No.: 13/518,146

(22) PCT Filed: Dec. 22, 2009

(86) PCT No.: PCT/EP2009/067784
§ 371 (c)(1),
(2), (4) Date: Sep. 17, 2012

(87) PCT Pub. No.: WO2011/076261
PCT Pub. Date: Jun. 30, 2011

(65) Prior Publication Data
US 2013/0052706 A1 Feb. 28, 2013

(51) Int. Cl.
*C12P 5/02* (2006.01)
*C12P 7/04* (2006.01)
*C12Q 1/00* (2006.01)
*C12N 9/00* (2006.01)
*C07H 21/04* (2006.01)
*C12P 5/00* (2006.01)

(52) U.S. Cl.
CPC .. *C12P 5/007* (2013.01); *C12P 7/04* (2013.01)

(58) Field of Classification Search
CPC ............ C12P 5/007; C12P 5/026; C12P 7/42; C12P 7/04; C12P 5/02; C12P 9/00; C12P 7/02; C12N 15/52; C12N 9/1029; C12Y 401/01033
See application file for complete search history.

(56) References Cited

U.S. PATENT DOCUMENTS

2005/0266518 A1* 12/2005 Berry et al. ................ 435/67

FOREIGN PATENT DOCUMENTS

CN 1491282 A 4/2004

OTHER PUBLICATIONS

Fisher et al. Non-radioactive assay for cellular dimethylallyl diphosphate, Analytical Biochemistry (2001), 292: 272-279.*
Kogan et al. Liquid phase isomerization of isoprenol into prenol in hydrogen environment, Applied Catalysis (2006), 297: 231-236.*
Whisstock et al. Quaterly Reviews of Biophysics, 2003, "Prediction of protein function from protein sequence and structure", 36(3): 307-340.*
Witkowski et al. Conversion of a beta-ketoacyl synthase to a malonyl decarboxylase by replacement of the active-site cysteine with glutamine, Biochemistry. Sep. 7, 1999;38(36):11643-50.*
Andreassi et al. (2004), Biochemistry 43: 16461-16466.*
Campos et al. *Escherichia coli* engineered to synthesize isopentenyl diphosphate and dimethylallyl diphosphate from mevalonate: a novel system for the genetic analysis of the 2-C-methyl-d-erythritol 4-phosphate pathway for isoprenoid biosynthesis, Biochem J. Jan. 1, 2001; 353(Pt 1):59-67.*
Office Action mailed Oct. 22, 2013 in China Application No. 200980163111.1, with translation.
The Activated Isoprene is Synthesized from Acetyl-CoA, Wikipedia, published on Sep. 16, 2009, with translation, 15 pgs.
Nabeta, K. et al. "Metabolism of RS-Mevalonic Acid-6,6,6-2H3 by in Vitro Callus Culture of *Perilla* sp.", Agricultural and Biological Chemistry, 1985, pp. 3039-3040, vol. 49, No. 10, XP002604884.
Jabalquinto, A.M. et al. "Substrate binding order in mevalonate 5-diphosphate decarboxylase from chicken liver", Biochimica Et Biophysica Acta. Protein Structure and Molecular Enzymology, 1989, pp. 257-259, vol. 996, No. 3, XP023579897.
Database UniProt [Online] Jul. 5, 2004, Fuetterer, O. et al.: "DE: Diphosphomevalonate decarboxylase; EC=4.1.1.33; OS: *Picrophilus torridus* (strain ATCC 700027 | DSM 9790 | JCM 10055 / NBRC100828)" XP002604885.
Database accession No. Q6KZB1 the whole document Database UniProt [Online] Oct. 1, 2001, Kawashima, T. et al.: "DE: Full=TVG0327166 protein; OS: *Thermoplasma volcanium* (strain ATCC 51530 | DSM 4299 IIFO 15438 / JCM 9571 / GSS1)" XP002604886 Database accession No. Q97BY2 the whole document.
Database UniProt [Online] Mar. 1, 2001, Ruepp, A. et al.: "DE: Full=Putative uncharacterized protein Ta1305; OS: Thermoplasma aci dophil um" XP002604887 | Database accession No. Q9HIN1 the whole document.
International Search Report, PCT/EP2009/067784, dated Feb. 25, 2011, 18 pgs.

* cited by examiner

*Primary Examiner* — Iqbal H Chowdhury
(74) *Attorney, Agent, or Firm* — Michele M. Wales; InHouse Patent Counsel, LLC

(57) ABSTRACT

Described is a method for the enzymatic production of isoprenol using mevalonate as a substrate and enzymatically converting it by a decarboxylation step into isoprenol as well as the use of an enzyme which is capable of catalyzing the decarboxylation of mevalonate for the production of isoprenol from mevalonate. Furthermore described is the use of mevalonate as a starting material for the production of isoprenol in an enzymatically catalyzed reaction. Also disclosed is a method for the production of isoprene comprising the method for the production of isoprenol using mevalonate as a substrate and enzymatically converting it by a decarboxylation step into isoprenol and further comprising the step of converting the produced isoprenol into isoprene as well as a method for the production of isoamyl alcohol comprising the method for the production of isoprenol using mevalonate as a substrate and enzymatically converting it by a decarboxylation step into isoprenol and further comprising the step of converting the produced isoprenol into isoamyl alcohol.

11 Claims, 6 Drawing Sheets

Phosphono-phosphate

Phosphonamido-phosphate

Figure 1:
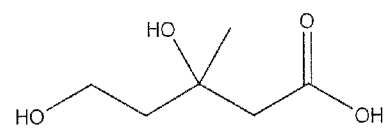

SEQUENCE LISTING

<160> NUMBER OF SEQ ID NOS: 22

<210> SEQ ID NO 1
<211> LENGTH: 400
<212> TYPE: PRT
<213> ORGANISM: Homo sapiens

<400> SEQUENCE: 1

Met Ala Ser Glu Lys Pro Leu Ala Ala Val Thr Cys Thr Ala Pro Val
1               5                   10                  15

Asn Ile Ala Val Ile Lys Tyr Trp Gly Lys Arg Asp Glu Glu Leu Val
            20                  25                  30

Leu Pro Ile Asn Ser Ser Leu Ser Val Thr Leu His Gln Asp Gln Leu
        35                  40                  45

Lys Thr Thr Thr Thr Ala Val Ile Ser Lys Asp Phe Thr Glu Asp Arg
    50                  55                  60

Ile Trp Leu Asn Gly Arg Glu Glu Asp Val Gly Gln Pro Arg Leu Gln
65                  70                  75                  80

Ala Cys Leu Arg Glu Ile Arg Cys Leu Ala Arg Lys Arg Arg Asn Ser
                85                  90                  95

Arg Asp Gly Asp Pro Leu Pro Ser Ser Leu Ser Cys Lys Val His Val
            100                 105                 110

Ala Ser Val Asn Asn Phe Pro Thr Ala Ala Gly Leu Ala Ser Ser Ala
        115                 120                 125

Ala Gly Tyr Ala Cys Leu Ala Tyr Thr Leu Ala Arg Val Tyr Gly Val
    130                 135                 140

Glu Ser Asp Leu Ser Glu Val Ala Arg Arg Gly Ser Gly Ser Ala Cys
145                 150                 155                 160

Arg Ser Leu Tyr Gly Gly Phe Val Glu Trp Gln Met Gly Glu Gln Ala
                165                 170                 175

Asp Gly Lys Asp Ser Ile Ala Arg Gln Val Ala Pro Glu Ser His Trp
            180                 185                 190

Pro Glu Leu Arg Val Leu Ile Leu Val Val Ser Ala Glu Lys Lys Leu
        195                 200                 205

Thr Gly Ser Thr Val Gly Met Arg Ala Ser Val Glu Thr Ser Pro Leu
    210                 215                 220

Leu Arg Phe Arg Ala Glu Ser Val Val Pro Ala Arg Met Ala Glu Met
225                 230                 235                 240

Ala Arg Cys Ile Arg Glu Arg Asp Phe Pro Ser Phe Ala Gln Leu Thr
                245                 250                 255

Met Lys Asp Ser Asn Gln Phe His Ala Thr Cys Leu Asp Thr Phe Pro
            260                 265                 270

Pro Ile Ser Tyr Leu Asn Ala Ile Ser Trp Arg Ile Ile His Leu Val
        275                 280                 285

His Arg Phe Asn Ala His His Gly Asp Thr Lys Val Ala Tyr Thr Phe

```
            290                 295                 300
Asp Ala Gly Pro Asn Ala Val Ile Phe Thr Leu Asp Asp Thr Val Ala
305                 310                 315                 320

Glu Phe Val Ala Ala Val Trp His Gly Phe Pro Pro Gly Ser Asn Gly
                325                 330                 335

Asp Thr Phe Leu Lys Gly Leu Gln Val Arg Pro Ala Pro Leu Ser Ala
            340                 345                 350

Glu Leu Gln Ala Ala Leu Ala Met Glu Pro Thr Pro Gly Gly Val Lys
        355                 360                 365

Tyr Ile Ile Val Thr Gln Val Gly Pro Gly Pro Gln Ile Leu Asp Asp
    370                 375                 380

Pro Cys Ala His Leu Leu Gly Pro Asp Gly Leu Pro Lys Pro Ala Ala
385                 390                 395                 400

<210> SEQ ID NO 2
<211> LENGTH: 396
<212> TYPE: PRT
<213> ORGANISM: Saccharomyces cerevisiae

<400> SEQUENCE: 2

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
    50                  55                  60

Gly Glu Pro His Ser Ile Asp Asn Glu Arg Thr Gln Asn Cys Leu Arg
65                  70                  75                  80

Asp Leu Arg Gln Leu Arg Lys Glu Met Glu Ser Lys Asp Ala Ser Leu
                85                  90                  95

Pro Thr Leu Ser Gln Trp Lys Leu His Ile Val Ser Glu Asn Asn Phe
            100                 105                 110

Pro Thr Ala Ala Gly Leu Ala Ser Ser Ala Ala Gly Phe Ala Ala Leu
        115                 120                 125

Val Ser Ala Ile Ala Lys Leu Tyr Gln Leu Pro Gln Ser Thr Ser Glu
    130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
        195                 200                 205

Thr Gln Gly Met Gln Leu Thr Val Ala Thr Ser Glu Leu Phe Lys Glu
    210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270
```

```
Tyr Met Asn Asp Thr Ser Lys Arg Ile Ile Ser Trp Cys His Thr Ile
            275                 280                 285

Asn Gln Phe Tyr Gly Glu Thr Ile Val Ala Tyr Thr Phe Asp Ala Gly
        290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
        355                 360                 365

Arg Val Ile Leu Thr Gln Val Gly Ser Gly Pro Gln Glu Thr Asn Glu
370                 375                 380

Ser Leu Ile Asp Ala Lys Thr Gly Leu Pro Lys Glu
385                 390                 395

<210> SEQ ID NO 3
<211> LENGTH: 404
<212> TYPE: PRT
<213> ORGANISM: Aspergillus niger

<400> SEQUENCE: 3

Met Ala Ala Ser Ala Asp Ser Gln Val Phe Arg Ala Thr Thr Thr Ala
1               5                   10                  15

Pro Val Asn Ile Ala Val Ile Lys Tyr Trp Gly Lys Arg Asp Ala Val
            20                  25                  30

Leu Asn Leu Pro Thr Asn Ser Ser Leu Ser Val Thr Leu Ser Gln Arg
        35                  40                  45

Ser Leu Arg Thr Leu Thr Thr Ala Ser Cys Ala Pro Phe Tyr Pro Ala
    50                  55                  60

Lys Asp Glu Leu Thr Leu Asn Gly Lys Pro Gln Asp Ile Gln Ser Ser
65                  70                  75                  80

Lys Arg Thr Leu Ala Cys Leu Ala Ser Leu Arg Ala His Arg Arg Glu
                85                  90                  95

Leu Glu Asp Ala Asn Pro Ser Leu Pro Lys Leu Ser Ser Phe Pro Leu
            100                 105                 110

Arg Ile Val Ser Glu Asn Asn Phe Pro Thr Ala Ala Gly Leu Ala Ser
        115                 120                 125

Ser Ala Ala Gly Phe Ala Ala Leu Val Arg Ala Val Ala Asp Leu Tyr
    130                 135                 140

Gln Leu Pro Gln Ser Pro Arg Asp Leu Ser Arg Ile Ala Arg Gln Gly
145                 150                 155                 160

Ser Gly Ser Ala Cys Arg Ser Leu Met Gly Gly Tyr Val Ala Trp Arg
                165                 170                 175

Ala Gly Ser Leu Glu Asp Gly Ser Asp Ser Leu Ala Glu Glu Val Ala
            180                 185                 190

Pro Gln Ser His Trp Pro Glu Met Arg Ala Leu Ile Leu Val Val Ser
        195                 200                 205

Ala Ala Lys Lys Asp Val Pro Ser Thr Glu Gly Met Gln Thr Thr Val
    210                 215                 220

Ala Thr Ser Asn Leu Phe Ala Thr Arg Ala Ser Thr Val Val Pro Glu
225                 230                 235                 240

Arg Met Ala Ala Ile Glu Thr Ala Ile Gln Asn Arg Asp Phe Pro Ala
                245                 250                 255
```

```
Phe Ala Glu Ile Thr Met Arg Asp Ser Asn Ser Phe His Ala Thr Cys
            260                 265                 270

Leu Asp Ser Trp Pro Pro Ile Phe Tyr Met Asn Asp Val Ser Arg Ala
        275                 280                 285

Ala Val Arg Leu Val His Asp Ile Asn Arg Ala Ile Gly Arg Thr Val
    290                 295                 300

Cys Ala Tyr Thr Tyr Asp Ala Gly Pro Asn Ala Val Ile Tyr Leu
305                 310                 315                 320

Glu Lys Asp Thr Glu Leu Val Ala Gly Thr Val Lys Ala Ile Leu Gly
                325                 330                 335

Glu Lys Thr Glu Gly Trp Glu Gly Pro Phe Tyr Thr Pro Leu Lys Asp
            340                 345                 350

Val Thr Thr Pro Gly Val Ser Leu Asp Glu Ile Asp Pro Arg Thr Val
        355                 360                 365

Glu Ser Leu Lys Asp Gly Val Ser Arg Val Ile Leu Thr Gly Val Gly
    370                 375                 380

Glu Gly Pro Ile Ser Val Asp Gln His Leu Val Ser Glu Lys Gly Asp
385                 390                 395                 400

Ile Leu Ser Ala

<210> SEQ ID NO 4
<211> LENGTH: 325
<212> TYPE: PRT
<213> ORGANISM: Lactobacillus platarum

<400> SEQUENCE: 4

Met Lys Thr Val Thr Ala Lys Ala His Thr Asn Ile Ala Leu Val Lys
1               5                   10                  15

Tyr Trp Gly Lys Lys Asp Ala Ala Leu Met Leu Pro Gln Asn Gly Ser
            20                  25                  30

Ile Ser Leu Thr Leu Asp His Phe Tyr Thr Gln Thr Ser Val Thr Phe
        35                  40                  45

Asp Glu His Leu Asp Thr Asp Gln Ile Tyr Phe Asn His Gln His Leu
    50                  55                  60

Pro Thr Gly Lys Ser Ala Arg Ile Ser Gln Phe Leu Asp Leu Ile Arg
65                  70                  75                  80

Gln Arg Ser Gly Gln Thr Asn Tyr Ala Thr Val Lys Thr Glu Asn His
                85                  90                  95

Val Pro Thr Ser Ala Gly Leu Ala Ser Ser Ala Ser Gly Phe Ala Ala
            100                 105                 110

Leu Ala Gly Ala Ala Ser Arg Ala Ala Gly Leu Gln Leu Asp Ala Ala
        115                 120                 125

Asp Leu Ser Arg Leu Ala Arg Arg Gly Ser Gly Ser Ala Thr Arg Ser
    130                 135                 140

Ile Phe Gly Gly Phe Val Glu Trp His Ala Gly His Asp Asp Gln Ser
145                 150                 155                 160

Ser Tyr Ala Glu Val Leu Gln Asp Pro Val Asp Trp Asp Ile Gln Met
                165                 170                 175

Ile Ala Val Val Leu Lys Ala Thr Lys Lys Thr Ile Ser Ser Thr Asp
            180                 185                 190

Gly Met Ala Arg Val Val Ala Thr Ser Pro Tyr Tyr Pro Ala Trp Ile
        195                 200                 205

Thr Thr Ala Glu Thr Asp Leu Lys Arg Met Arg Gln Ala Ile Ala Asp
    210                 215                 220
```

```
Arg Asp Leu Thr Thr Val Gly Gln Ile Ala Glu Thr Asn Ala Met Arg
225                 230                 235                 240

Met His Ala Leu Asn Leu Ser Ala Glu Pro Ala Phe Asn Tyr Phe Thr
                245                 250                 255

Ala Asp Thr Leu Thr Ala Ile Gln Ala Val Asn Asp Leu Arg Ser His
            260                 265                 270

Gly Ile Asn Cys Tyr Tyr Thr Leu Asp Ala Gly Pro Asn Val Lys Ile
        275                 280                 285

Ile Cys Ala Gly Gln Asp Thr Asp Thr Ile Met Thr Gly Leu Gln Gln
    290                 295                 300

His Phe Asp Ala Asp Gln Leu Ile Val Ala Lys Pro Gly Pro Gly Ile
305                 310                 315                 320

Thr Ile Thr Glu Lys
                325

<210> SEQ ID NO 5
<211> LENGTH: 314
<212> TYPE: PRT
<213> ORGANISM: Streptococcus pyrogenes

<400> SEQUENCE: 5

Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
                20                  25                  30

Ser Ser Ile Ser Leu Thr Leu Glu Asn Met Phe Thr Thr Thr Ser Val
            35                  40                  45

Ser Phe Leu Pro Asp Thr Ala Thr Ser Asp Gln Phe Tyr Ile Asn Gly
        50                  55                  60

Ile Leu Gln Asn Asp Glu His Thr Lys Ile Ser Ala Ile Ile Asp
65                  70                  75                  80

Gln Phe Arg Gln Pro Gly Gln Ala Phe Val Lys Met Glu Thr Gln Asn
                85                  90                  95

Asn Met Pro Thr Ala Ala Gly Leu Ser Ser Ser Ser Gly Leu Ser
                100                 105                 110

Ala Leu Val Lys Ala Cys Asp Gln Leu Phe Asp Thr Gln Leu Asp Gln
            115                 120                 125

Lys Ala Leu Ala Gln Lys Ala Lys Phe Ala Ser Gly Ser Ser Ser Arg
        130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
                165                 170                 175

Asn Ala Ala Lys Lys Pro Ile Ser Ser Arg Glu Gly Met Lys Leu Cys
            180                 185                 190

Arg Asp Thr Ser Thr Thr Phe Asp Gln Trp Val Glu Gln Ser Ala Ile
        195                 200                 205

Asp Tyr Gln His Met Leu Thr Tyr Leu Lys Thr Asn Asn Phe Glu Lys
    210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Thr Lys Glu Ser Tyr Gln
                245                 250                 255

Ala Met Glu Ala Val Lys Glu Leu Arg Gln Glu Gly Phe Ala Cys Tyr
```

```
                260                 265                 270
Phe Thr Met Asp Ala Gly Pro Asn Val Lys Val Leu Cys Leu Glu Lys
            275                 280                 285
Asp Leu Ala Gln Leu Ala Glu Arg Leu Gly Lys Asn Tyr Arg Ile Ile
            290                 295                 300
Val Ser Lys Thr Lys Asp Leu Pro Asp Val
305                 310

<210> SEQ ID NO 6
<211> LENGTH: 324
<212> TYPE: PRT
<213> ORGANISM: Picrophilus torridus
<220> FEATURE:
<223> OTHER INFORMATION: DSM 9790

<400> SEQUENCE: 6

Met Glu Asn Tyr Asn Val Lys Thr Arg Ala Phe Pro Thr Ile Gly Ile
1               5                   10                  15

Ile Leu Gly Gly Ile Ser Asp Lys Lys Asn Arg Ile Pro Leu His
            20                  25                  30

Thr Thr Ala Gly Ile Ala Tyr Thr Gly Ile Asn Asn Asp Val Tyr Thr
            35                  40                  45

Glu Thr Lys Leu Tyr Val Ser Lys Asp Glu Lys Cys Tyr Ile Asp Gly
    50                  55                  60

Lys Glu Ile Asp Leu Asn Ser Asp Arg Ser Pro Ser Lys Val Ile Asp
65                  70                  75                  80

Lys Phe Lys His Glu Ile Leu Met Arg Val Asn Leu Asp Asp Glu Asn
                85                  90                  95

Asn Leu Ser Ile Asp Ser Arg Asn Phe Asn Ile Leu Ser Gly Ser Ser
            100                 105                 110

Asp Ser Gly Ala Ala Ala Leu Gly Glu Cys Ile Glu Ser Ile Phe Glu
            115                 120                 125

Tyr Asn Ile Asn Ile Phe Thr Phe Glu Asn Asp Leu Gln Arg Ile Ser
            130                 135                 140

Glu Ser Val Gly Arg Ser Leu Tyr Gly Gly Leu Thr Val Asn Tyr Ala
145                 150                 155                 160

Asn Gly Arg Glu Ser Leu Thr Glu Pro Leu Leu Glu Pro Glu Ala Phe
                165                 170                 175

Asn Asn Phe Thr Ile Ile Gly Ala His Phe Asn Ile Asp Arg Lys Pro
            180                 185                 190

Ser Asn Glu Ile His Glu Asn Ile Ile Lys His Glu Asn Tyr Arg Glu
            195                 200                 205

Arg Ile Lys Ser Ala Glu Arg Lys Ala Lys Leu Glu Glu Leu Ser
    210                 215                 220

Arg Asn Ala Asn Ile Lys Gly Ile Phe Glu Leu Ala Glu Ser Asp Thr
225                 230                 235                 240

Val Glu Tyr His Lys Met Leu His Asp Val Gly Val Asp Ile Ile Asn
                245                 250                 255

Asp Arg Met Glu Asn Leu Ile Glu Arg Val Lys Glu Met Lys Asn Asn
            260                 265                 270

Phe Trp Asn Ser Tyr Ile Val Thr Gly Gly Pro Asn Val Phe Val Ile
            275                 280                 285

Thr Glu Lys Lys Asp Val Asp Lys Ala Met Glu Gly Leu Asn Asp Leu
            290                 295                 300

Cys Asp Asp Ile Arg Leu Leu Lys Val Ala Gly Lys Pro Gln Val Ile
```

Ser Lys Asn Phe

<210> SEQ ID NO 7
<211> LENGTH: 319
<212> TYPE: PRT
<213> ORGANISM: Lactobacillus delbrueckii
<220> FEATURE:
<223> OTHER INFORMATION: subsp. bulgaricus

<400> SEQUENCE: 7

Met Ser Lys Thr Ala Arg Ala His Thr Asn Ile Ala Leu Ile Lys Tyr
1               5                   10                  15

Trp Gly Lys Lys Asp Ala Lys Leu Arg Leu Pro Leu Met Ser Ser Leu
                20                  25                  30

Ser Met Thr Leu Asp Ala Phe Tyr Ser Asp Thr Lys Ile Ser Asp Ser
            35                  40                  45

Glu Gln Met Ser Phe Lys Leu Asn Gly Gln Ala Val Ser Gly Pro Ala
        50                  55                  60

Ala Asp Arg Val Phe Ala Tyr Leu Arg Ala Met Gln Asp Arg Phe Gly
65                  70                  75                  80

Val Lys Gly Asn Leu Ala Val Glu Ser Val Asn Gln Val Pro Thr Ala
                85                  90                  95

Ala Gly Leu Ala Ser Ser Ser Ala Phe Ala Met Ala Ala Ala
            100                 105                 110

Phe Ala Asp His Tyr Gln Leu Gly Val Asp Arg Gln Glu Leu Ser Arg
            115                 120                 125

Met Ala Arg Met Gly Ser Gly Ser Ala Ser Arg Ser Val Phe Gly Gly
        130                 135                 140

Phe Ser Val Trp Gln Lys Gly Asp Ser Asp Gln Thr Ser Tyr Ala Tyr
145                 150                 155                 160

Pro Leu Asp Glu Glu Pro Asp Met Asp Leu Arg Leu Leu Ala Val Glu
                165                 170                 175

Ile Asn Asp Gln Glu Lys Lys Ile Ser Ser Thr Lys Gly Met Glu Met
            180                 185                 190

Ser Lys Ser Ser Pro Phe Tyr Gln Val Trp Leu Asp Arg Asn Asp Ser
        195                 200                 205

Glu Ile Lys Glu Met Glu Glu Ala Ile Lys Gln Ala Asp Phe Ser Lys
    210                 215                 220

Leu Gly Ser Leu Ala Glu Leu Asn Ala Ser Glu Met His Thr Leu Thr
225                 230                 235                 240

Phe Thr Ala Val Pro Gly Phe Thr Tyr Phe Glu Pro Asn Thr Ile Lys
                245                 250                 255

Ala Ile Lys Leu Val Gln Asp Leu Arg Gln Gly Leu Glu Cys Tyr
            260                 265                 270

Tyr Thr Ile Asp Ala Gly Pro Asn Val Lys Val Leu Cys Gln Gly Lys
        275                 280                 285

Asn Ser Lys Asp Ile Ile Asn Cys Phe Glu Ser Ser Phe Asp Arg Val
    290                 295                 300

Lys Ile Ile Glu Ala Gly Phe Gly Pro Gly Val Thr Leu Leu Asp
305                 310                 315

<210> SEQ ID NO 8
<211> LENGTH: 324
<212> TYPE: PRT
<213> ORGANISM: Haloquadratum walsbyi

<220> FEATURE:
<223> OTHER INFORMATION: DSM 16790

<400> SEQUENCE: 8

Met Lys Ala Thr Ala Arg Ala His Pro Ile Gln Gly Leu Ile Lys Tyr
1               5                   10                  15

His Gly Met Arg Asp Ser Asp Lys Arg Tyr Pro Tyr His Asp Ser Ile
            20                  25                  30

Ser Val Cys Thr Ala Pro Ser Ala Thr Thr Thr Val Glu Phe Gln
        35                  40                  45

Ser Asp Ala Ser Gly Asp Val Tyr Ile Ile Asp Asn Glu Arg Val Asp
50                  55                  60

Gly Arg Ala Ala Glu Arg Ile Asp Ala Val Val Glu His Val Arg Glu
65                  70                  75                  80

Arg Thr Gly Ile Arg Asp Pro Val Arg Leu Val Ser Thr Asn Ser Phe
                85                  90                  95

Pro Ser Asn Ile Gly Phe Gly Ser Ser Ser Gly Phe Ala Ala Ala
            100                 105                 110

Ala Met Ala Leu Val Thr Ala Ala Gly Glu Glu Leu Thr His Pro Glu
        115                 120                 125

Ile Ser Thr Ile Ala Arg Arg Gly Ser Ser Ala Ala Arg Ala Val
130                 135                 140

Thr Gly Ala Phe Ser Gln Leu Tyr Ser Gly Met Asn Asp Thr Asp Cys
145                 150                 155                 160

His Ala Glu Arg Ile Glu Thr Asp Leu Asp Ala Thr Val Arg Thr Val
                165                 170                 175

Ala Ala His Val Pro Ala Tyr Lys Glu Thr Glu Ala His Arg Glu
            180                 185                 190

Ala Ala Gln Ser His Met Phe Asp Ala Arg Leu Ala His Val His His
        195                 200                 205

Gln Ile Asp Ala Met Arg Asp Ala Leu Tyr Asn Ala Asp Phe Asp Arg
210                 215                 220

Ile Phe Glu Leu Ala Glu His Asp Ser Leu Ser Leu Thr Ala Ala Thr
225                 230                 235                 240

Met Thr Gly Pro Ala Gly Trp Val Tyr Trp Gln Pro Gln Thr Ile Ala
                245                 250                 255

Val Phe Asn Thr Val Arg Glu Leu Arg Glu Arg Glu Ser Ile Pro Val
            260                 265                 270

Tyr Phe Ser Thr Asp Thr Gly Ala Ser Val Tyr Val Asn Thr Thr Ala
        275                 280                 285

Ala His Val Asp Thr Val Glu Ser Ala Ile Ser Asp Ile Gly Ile Asp
290                 295                 300

Thr Asp Ile Trp Thr Val Gly Gly Pro Ala Thr Val Leu Ser Ala Ser
305                 310                 315                 320

Asp Ser Leu Phe

<210> SEQ ID NO 9
<211> LENGTH: 322
<212> TYPE: PRT
<213> ORGANISM: Lactobacillus salivarius
<220> FEATURE:
<223> OTHER INFORMATION: subsp. salivarius (strain UCC118)

<400> SEQUENCE: 9

Met Ser Asn His Ala Ala Ala Arg Ala His Thr Asn Ile Ala Leu Ile
1               5                   10                  15

```
Lys Tyr Trp Gly Lys Lys Asp Thr Glu Leu Ile Leu Pro Met Asn Asn
            20                  25                  30

Ser Leu Ser Leu Thr Leu Asp His Phe Tyr Thr Asp Thr Ser Val Thr
        35                  40                  45

Phe Asp Ser Ser Tyr Thr Lys Asp Thr Phe Ile Leu Asn Gly Lys Glu
 50                  55                  60

Ile Pro Asn Glu Asn Val His Lys Phe Leu Asn Ile Val Arg Glu Lys
 65                  70                  75                  80

Ala Gly Ile Ser Glu Phe Ala Lys Val Asn Ser Thr Asn His Val Pro
                85                  90                  95

Thr Thr Ala Gly Leu Ala Ser Ser Ala Ser Phe Ala Ala Leu Ala
            100                 105                 110

Ala Ala Ala Ser Lys Ala Ser Gly Met Asn Leu Ser Arg Arg Asp Leu
            115                 120                 125

Ser Arg Leu Ala Arg Arg Gly Ser Gly Ser Ala Thr Arg Ser Ile Tyr
        130                 135                 140

Gly Gly Phe Val Glu Trp Gln Ala Gly Asp Asn Asp Leu Asn Ser Tyr
145                 150                 155                 160

Ala Val Pro Phe Ile Glu Asn Val Ser Trp Asp Ile Lys Met Ile Ala
                165                 170                 175

Val Val Ile Asn Ser Lys Pro Lys Ile Thr Ser Arg Ala Gly Met
                180                 185                 190

Gln Thr Val Val Asn Thr Ser Pro Tyr Tyr Asn Ser Trp Ile Lys Glu
        195                 200                 205

Ala Asn Arg Ser Ile Pro Leu Met Lys Glu Ala Ile Ser Lys Gln Asp
        210                 215                 220

Phe Thr Thr Met Gly Glu Leu Ala Glu Asn Ala Met Lys Met His
225                 230                 235                 240

Ala Leu Asn Leu Ser Ala His Pro His Phe Ser Tyr Phe Ser Pro Glu
                245                 250                 255

Ser Ile Gln Val Met Asn Leu Val Glu Glu Leu Arg Ser Met Gly Ile
            260                 265                 270

Glu Cys Tyr Tyr Thr Met Asp Ala Gly Pro Asn Val Lys Ile Ile Cys
            275                 280                 285

Leu Gly Lys Asp Thr Ala Ser Ile Thr Ser Phe Leu Gln Lys Asn Leu
        290                 295                 300

Pro Asn Thr Glu Val Leu Val Ser Ser Ala Gly Pro Gly Val Gln Tyr
305                 310                 315                 320

Leu Asp

<210> SEQ ID NO 10
<211> LENGTH: 314
<212> TYPE: PRT
<213> ORGANISM: Oenococcus oeni
<220> FEATURE:
<223> OTHER INFORMATION: (strain BAA-331 / PSU-1)

<400> SEQUENCE: 10

Met Ala Lys Val Arg Ala Tyr Thr Asn Ile Ala Leu Ile Lys Tyr Trp
 1               5                  10                  15

Gly Lys Ser Asp Leu Asn Trp Asn Leu Pro Thr Ser Ser Ile Gly
            20                  25                  30

Leu Thr Leu Asp Arg Phe Tyr Asp Thr Ser Val Glu Ile Asp Gln
        35                  40                  45
```

```
Phe Ser Lys Lys Asp Phe Phe Gln Leu Asn Gly Gln Gln Ile Glu Gly
 50                  55                  60
Pro Lys Ile Ser Lys Ile Ile Asn Phe Ile Arg Asn Ser Cys Gly Asn
 65                  70                  75                  80
Lys Asn Phe Val Lys Val Ile Ser Glu Asn His Val Pro Thr Ser Ala
                 85                  90                  95
Gly Leu Ala Ser Ser Ala Ser Ala Phe Ala Ala Leu Thr Lys Ala Ala
                100                 105                 110
Asn Gln Ala Phe Gly Leu Glu Leu Asp Asn Arg Glu Leu Ser Lys Ile
                115                 120                 125
Ala Arg Ile Gly Ser Gly Ser Ala Ser Arg Ser Ile Phe Gly Gly Phe
            130                 135                 140
Ser Ile Trp His Lys Gly Gln Asn Lys Asp Asp Ser Phe Ala Glu Ser
145                 150                 155                 160
Ile Leu Asp Pro Val Asp Phe Asp Ile Arg Val Ile Asp Ile Leu Ala
                165                 170                 175
Asp Lys Arg Val Lys Lys Ile Ser Ser Ser Gln Gly Met Gln Leu Ala
                180                 185                 190
Gln Thr Ser Pro Asn Tyr Asp Ser Trp Leu Lys Lys Asn Asp Arg Gln
            195                 200                 205
Ile Asp Glu Met Leu Lys Ala Ile Ser Asp His Asp Leu Glu Lys Ile
        210                 215                 220
Gly Leu Ile Ala Glu Thr Asn Ser Ala Ser Met His Glu Leu Asn Arg
225                 230                 235                 240
Thr Ala Lys Val Pro Phe Asp Tyr Phe Thr Glu Asn Thr Arg Glu Ile
                245                 250                 255
Ile Ala Glu Val Asp Gln Leu Tyr Lys Lys Gly Ile Leu Ala Phe Ala
                260                 265                 270
Thr Val Asp Ala Gly Pro Asn Val Lys Val Ile Thr Asn Ser Glu Tyr
            275                 280                 285
Gln Glu Lys Ile Ile Asn Val Leu Lys Glu Tyr Gly Glu Ile Leu Val
        290                 295                 300
Gln Lys Pro Gly Arg Gly Val Ala Asn Val
305                 310

<210> SEQ ID NO 11
<211> LENGTH: 327
<212> TYPE: PRT
<213> ORGANISM: Pediococcus pentosaceus
<220> FEATURE:
<223> OTHER INFORMATION: ATCC 25745

<400> SEQUENCE: 11

Met Asn Glu Lys His Gly Phe Ala Arg Ala His Thr Asn Ile Ala Leu
 1                5                  10                  15
Leu Lys Tyr Trp Gly Lys Ile Asn Ser Asp Leu Ile Leu Pro Ala Asn
                 20                  25                  30
Asp Ser Ile Ser Leu Thr Leu Asp Lys Phe Tyr Thr Asp Thr Glu Val
             35                  40                  45
Thr Phe Ser Asp Glu Tyr Thr Ser Asn Leu Phe Tyr Leu Asn His Gln
 50                  55                  60
Leu Ile Asp Val Lys Lys Met Gln Arg Ile Asn Arg Val Leu Glu Ala
 65                  70                  75                  80
Val Lys Ser Glu Phe Gly Tyr Gln Gly Phe Ala Lys Ile Glu Ser Glu
                 85                  90                  95
```

```
Asn His Val Pro Thr Ala Ala Gly Leu Ala Ser Ser Ala Ser Gly Met
            100                 105                 110

Ala Ala Leu Ala Gly Ala Ala Val Ser Ala Leu Gly Ser His Thr Asp
        115                 120                 125

Leu Thr Asn Leu Ser Arg Leu Ala Arg Leu Gly Ser Gly Ser Ala Ser
130                 135                 140

Arg Ser Val Phe Gly Gly Ile Val His Trp His Arg Gly Tyr Asp His
145                 150                 155                 160

Gln Ser Ser Phe Ala Glu Gln Ile Val Ser Glu Asp Gln Ile Asp Leu
                165                 170                 175

Asn Met Val Thr Ile Val Ile Asp Arg Arg Gln Lys Lys Val Lys Ser
            180                 185                 190

Thr Leu Gly Met Gln His Thr Ala Ser Thr Ser Pro Phe Tyr Pro Ala
        195                 200                 205

Trp Val Glu Ala Thr Asn Gln Ala Ile Pro Glu Met Ile Ser Ala Val
    210                 215                 220

Gln Asn Asn Asp Phe Thr Lys Ile Gly Glu Leu Ala Glu His Ser Ala
225                 230                 235                 240

Ala Met Met His Ala Thr Thr Leu Ser Ser Lys Pro Ala Phe Thr Tyr
                245                 250                 255

Phe Ala Pro Glu Thr Ile Gln Ala Ile Lys Leu Val Glu Gln Leu Arg
            260                 265                 270

Glu Ser Gly Ile Glu Cys Tyr Tyr Thr Ile Asp Ala Gly Pro Asn Val
        275                 280                 285

Lys Val Leu Cys Gln Ser Lys Asn Ile Thr Arg Val Lys Arg Phe Phe
290                 295                 300

Ala Ser Tyr Phe Asp Gln Asp Gln Leu Val Val Ala Lys Pro Gly Ser
305                 310                 315                 320

Gly Ile Lys Phe Thr Lys Asn
                325

<210> SEQ ID NO 12
<211> LENGTH: 315
<212> TYPE: PRT
<213> ORGANISM: Streptococcus gordonii

<400> SEQUENCE: 12

Met Asp Arg Lys Pro Val Ser Val Lys Ser Tyr Ala Asn Ile Ala Ile
1               5                   10                  15

Val Lys Tyr Trp Gly Lys Lys Asp Ala Glu Lys Met Ile Pro Ser Thr
            20                  25                  30

Ser Ser Ile Ser Leu Thr Leu Glu Asn Met Tyr Thr Glu Thr Gln Leu
        35                  40                  45

Ser Pro Leu Pro Asp Thr Ala Thr Gly Asp Glu Phe Tyr Ile Asp Gly
    50                  55                  60

Gln Leu Gln Ser Pro Ala Glu His Ala Lys Ile Ser Lys Ile Ile Asp
65                  70                  75                  80

Arg Phe Arg Ser Pro Glu Asp Gly Phe Val Arg Val Asp Thr Ser Asn
                85                  90                  95

Asn Met Pro Thr Ala Ala Gly Leu Ser Ser Ser Ser Gly Leu Ser
            100                 105                 110

Ala Leu Val Lys Ala Cys Asn Ala Tyr Phe Gln Thr Gly Tyr Gln Thr
        115                 120                 125

Glu Glu Leu Ala Gln Leu Ala Lys Phe Ala Ser Gly Ser Ser Ala Arg
    130                 135                 140
```

```
Ser Phe Phe Gly Pro Leu Ala Ala Trp Asp Lys Asp Ser Gly Ala Ile
145                 150                 155                 160

Tyr Pro Val Lys Thr Asp Leu Lys Leu Ala Met Ile Met Leu Val Leu
            165                 170                 175

His Asp Glu Lys Lys Pro Ile Ser Ser Arg Asp Gly Met Glu Leu Cys
        180                 185                 190

Ala Lys Thr Ser Thr Ile Phe Pro Asp Trp Ile Ala Gln Ser Ala Leu
    195                 200                 205

Asp Tyr Gln Ala Met Leu Gly Tyr Leu Gln Asp Asn Asp Phe Ala Lys
210                 215                 220

Val Gly Gln Leu Thr Glu Glu Asn Ala Leu Arg Met His Ala Thr Thr
225                 230                 235                 240

Glu Lys Ala Tyr Pro Pro Phe Ser Tyr Leu Thr Glu Glu Ser Tyr Gln
            245                 250                 255

Ala Met Asp Ala Val Arg Lys Leu Arg Glu Gln Gly Glu Arg Cys Tyr
        260                 265                 270

Phe Thr Met Asp Ala Gly Pro Asn Val Lys Val Leu Cys Leu Glu Glu
    275                 280                 285

Asp Leu Asp His Leu Ala Ala Ile Phe Glu Lys Asp Tyr Arg Leu Ile
290                 295                 300

Val Ser Lys Thr Lys Asp Leu Ser Asp Glu Ser
305                 310                 315

<210> SEQ ID NO 13
<211> LENGTH: 328
<212> TYPE: PRT
<213> ORGANISM: Dichelobacter nodosus
<220> FEATURE:
<223> OTHER INFORMATION: VCS1703A

<400> SEQUENCE: 13

Met His Ser Ala Thr Ala Phe Ala Pro Ala Asn Ile Ala Leu Ala Lys
1               5                   10                  15

Tyr Trp Gly Lys Arg Asp Ala Gln Leu Asn Leu Pro Thr Asn Gly Ser
            20                  25                  30

Leu Ser Ile Ser Leu Ala His Leu Gly Thr Thr Thr Ile Ser Ala
        35                  40                  45

Gly Glu Arg Asp Gln Leu Tyr Cys Asp His Arg Leu Leu Pro Pro Asp
    50                  55                  60

Thr Ala Phe Val Gln Lys Val Trp His Phe Ile Asp Phe Cys Gln Pro
65                  70                  75                  80

Lys Arg Pro Pro Leu Val Ile His Thr Gln Asn Asn Ile Pro Thr Ala
            85                  90                  95

Ala Gly Leu Ala Ser Ser Ala Ser Gly Phe Ala Ala Leu Thr Leu Ala
        100                 105                 110

Leu Asn Asp Phe Phe Gln Trp Ser Leu Ser Arg Glu Gln Leu Ser Gln
    115                 120                 125

Ile Ala Arg Arg Gly Ser Gly Ser Ala Cys Arg Ser Leu Trp Gln Gly
130                 135                 140

Phe Val Tyr Trp Gln Lys Gly Glu Lys Ala Asp Gly Ser Asp Cys Tyr
145                 150                 155                 160

Ala Arg Pro Ile Ala Ser Asp Trp Gln Asp Leu Arg Leu Gly Ile Ile
            165                 170                 175

Thr Ile Asp Ala Ala Ala Lys Lys Ile Ser Ser Arg Gln Ala Met Asn
        180                 185                 190
```

```
His Thr Ala Ala Ser Ser Pro Leu Phe Ser Ser Trp Thr Gln Ala Ala
            195                 200                 205

Glu Ala Asp Leu Lys Val Ile Tyr Gln Ala Val Leu Asp Arg Asp Phe
    210                 215                 220

Leu Thr Leu Ala Gln Thr Ala Glu Ala Asn Ala Leu Met Met His Ala
225                 230                 235                 240

Ser Leu Leu Ala Ala Arg Pro Ala Ile Phe Tyr Trp Gln Pro Gln Thr
                245                 250                 255

Leu Ala Met Leu Gln Cys Ile Trp Gln Ala Arg Ala Glu Gly Leu Ala
            260                 265                 270

Val Tyr Ala Thr Leu Asp Ala Gly Ala Asn Val Lys Leu Leu Tyr Arg
            275                 280                 285

Ala Gln Asp Glu Ala Glu Ile Ala Ser Met Phe Pro Gln Ala Gln Leu
        290                 295                 300

Ile Asn Pro Phe Gln Thr Val Thr Ser Ser Ala Arg His Thr Gly Glu
305                 310                 315                 320

Asp Ala Gln Lys Pro Ser Leu Lys
            325

<210> SEQ ID NO 14
<211> LENGTH: 317
<212> TYPE: PRT
<213> ORGANISM: Streptococcus pneumoniae
<220> FEATURE:
<223> OTHER INFORMATION: CDC0288-04

<400> SEQUENCE: 14

Met Asp Arg Glu Pro Val Thr Val Arg Ser Tyr Ala Asn Ile Ala Ile
1               5                   10                  15

Ile Lys Tyr Trp Gly Lys Lys Lys Glu Lys Met Val Pro Ala Thr
            20                  25                  30

Ser Ser Ile Ser Leu Thr Leu Glu Asn Met Tyr Thr Glu Thr Thr Leu
        35                  40                  45

Ser Pro Leu Pro Ala Asn Val Thr Ala Asp Glu Phe Tyr Ile Asn Gly
    50                  55                  60

Gln Leu Gln Asn Glu Val Glu His Ala Lys Met Ser Lys Ile Ile Asp
65                  70                  75                  80

Arg Tyr Arg Pro Ala Gly Glu Gly Phe Val Arg Ile Asp Thr Gln Asn
                85                  90                  95

Asn Met Pro Thr Ala Ala Gly Leu Ser Ser Ser Ser Ser Gly Leu Ser
            100                 105                 110

Ala Leu Val Lys Ala Cys Asn Ala Tyr Phe Lys Leu Gly Leu Asp Arg
        115                 120                 125

Ser Gln Leu Ala Gln Glu Ala Lys Phe Ala Ser Gly Ser Ser Ser Arg
    130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
                165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
    210                 215                 220
```

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
            245                 250                 255

Ala Met Ala Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
        275                 280                 285

Asp Leu Glu His Leu Ser Glu Ile Phe Gly Gln Arg Tyr Arg Leu Ile
        290                 295                 300

Val Ser Lys Thr Lys Asp Leu Ser Gln Asp Asp Cys Cys
305                 310                 315

<210> SEQ ID NO 15
<211> LENGTH: 314
<212> TYPE: PRT
<213> ORGANISM: Streptococcus pyogenes
<220> FEATURE:
<223> OTHER INFORMATION: serotype M6 (ATCC BAA-946 / MGAS10394)

<400> SEQUENCE: 15

Met Asp Pro Asn Val Ile Thr Val Thr Ser Tyr Ala Asn Ile Ala Ile
1               5                   10                  15

Ile Lys Tyr Trp Gly Lys Glu Asn Gln Ala Lys Met Ile Pro Ser Thr
            20                  25                  30

Ser Ser Ile Ser Leu Thr Leu Glu Asn Met Phe Thr Thr Thr Ser Val
        35                  40                  45

Ser Phe Leu Pro Asp Thr Ala Thr Ser Asp Gln Phe Tyr Ile Asn Gly
    50                  55                  60

Val Leu Gln Asn Asp Glu Glu His Thr Lys Ile Ser Ala Ile Ile Asp
65                  70                  75                  80

Gln Phe Arg Gln Pro Gly Gln Ala Phe Val Lys Met Glu Thr Gln Asn
            85                  90                  95

Asn Met Pro Thr Ala Ala Gly Leu Ser Ser Ser Ser Gly Leu Ser
            100                 105                 110

Ala Leu Val Lys Ala Cys Asp Gln Leu Phe Asn Thr Gln Leu Asp Gln
        115                 120                 125

Lys Ala Leu Ala Gln Lys Ala Lys Phe Ala Ser Gly Ser Ser Ser Arg
    130                 135                 140

Ser Phe Phe Gly Pro Val Ala Ala Trp Asp Lys Asp Ser Gly Ala Ile
145                 150                 155                 160

Tyr Lys Val Glu Thr Asp Leu Lys Met Ala Met Ile Met Leu Val Leu
            165                 170                 175

Asn Ala Ala Lys Lys Pro Ile Ser Ser Arg Glu Gly Met Lys Leu Cys
            180                 185                 190

Arg Asp Thr Ser Thr Thr Phe Asp Glu Trp Val Glu Gln Ser Ala Ile
        195                 200                 205

Asp Tyr Gln His Met Leu Thr Tyr Leu Lys Thr Asn Asn Phe Glu Lys
    210                 215                 220

Val Gly Gln Leu Thr Glu Ala Asn Ala Leu Ala Met His Ala Thr Thr
225                 230                 235                 240

Lys Thr Ala Asn Pro Pro Phe Ser Tyr Leu Lys Glu Ser Tyr Gln
            245                 250                 255

Ala Met Glu Ala Val Lys Glu Leu Arg Gln Glu Gly Phe Ala Cys Tyr
            260                 265                 270

```
Phe Thr Met Asp Ala Gly Pro Asn Val Lys Val Leu Cys Leu Glu Lys
            275                 280                 285

Asp Leu Ala Gln Leu Ala Glu Arg Leu Gly Lys Asn Tyr Arg Ile Ile
        290                 295                 300

Val Ser Lys Thr Lys Asp Leu Pro Asp Val
305                 310

<210> SEQ ID NO 16
<211> LENGTH: 330
<212> TYPE: PRT
<213> ORGANISM: Picrophilus torridus
<220> FEATURE:
<223> OTHER INFORMATION: DSM 9790

<400> SEQUENCE: 16

Met His His His His His Glu Asn Tyr Asn Val Lys Thr Arg Ala
1               5                   10                  15

Phe Pro Thr Ile Gly Ile Ile Leu Leu Gly Ile Ser Asp Lys Lys
            20                  25                  30

Asn Arg Ile Pro Leu His Thr Thr Ala Gly Ile Ala Tyr Thr Gly Ile
            35                  40                  45

Asn Asn Asp Val Tyr Thr Glu Thr Lys Leu Tyr Val Ser Lys Asp Glu
        50                  55                  60

Lys Cys Tyr Ile Asp Gly Lys Glu Ile Asp Leu Asn Ser Asp Arg Ser
65                  70                  75                  80

Pro Ser Lys Val Ile Asp Lys Phe Lys His Glu Ile Leu Met Arg Val
                85                  90                  95

Asn Leu Asp Asp Glu Asn Asn Leu Ser Ile Asp Ser Arg Asn Phe Asn
            100                 105                 110

Ile Leu Ser Gly Ser Ser Asp Ser Gly Ala Ala Ala Leu Gly Glu Cys
            115                 120                 125

Ile Glu Ser Ile Phe Glu Tyr Asn Ile Asn Ile Phe Thr Phe Glu Asn
            130                 135                 140

Asp Leu Gln Arg Ile Ser Glu Ser Val Gly Arg Ser Leu Tyr Gly Gly
145                 150                 155                 160

Leu Thr Val Asn Tyr Ala Asn Gly Arg Glu Ser Leu Thr Glu Pro Leu
                165                 170                 175

Leu Glu Pro Glu Ala Phe Asn Asn Phe Thr Ile Ile Gly Ala His Phe
            180                 185                 190

Asn Ile Asp Arg Lys Pro Ser Asn Glu Ile His Glu Asn Ile Ile Lys
            195                 200                 205

His Glu Asn Tyr Arg Glu Arg Ile Lys Ser Ala Glu Arg Lys Ala Lys
        210                 215                 220

Lys Leu Glu Glu Leu Ser Arg Asn Ala Asn Lys Gly Ile Phe Glu
225                 230                 235                 240

Leu Ala Glu Ser Asp Thr Val Glu Tyr His Lys Met Leu His Asp Val
                245                 250                 255

Gly Val Asp Ile Ile Asn Asp Arg Met Glu Asn Leu Ile Glu Arg Val
            260                 265                 270

Lys Glu Met Lys Asn Asn Phe Trp Asn Ser Tyr Ile Val Thr Gly Gly
            275                 280                 285

Pro Asn Val Phe Val Ile Thr Glu Lys Lys Asp Val Asp Lys Ala Met
        290                 295                 300

Glu Gly Leu Asn Asp Leu Cys Asp Ile Arg Leu Leu Lys Val Ala
305                 310                 315                 320
```

```
Gly Lys Pro Gln Val Ile Ser Lys Asn Phe
            325                 330

<210> SEQ ID NO 17
<211> LENGTH: 327
<212> TYPE: PRT
<213> ORGANISM: Thermoplasma volcanium

<400> SEQUENCE: 17

Met Leu His His His His His His Ser Asn Ser Ser Ile Thr Ser Val
1               5                   10                  15

Ala Tyr Pro Thr Ile Gly Val Val Leu Leu Gly Gly Ile Ala Asn Glu
            20                  25                  30

Lys Thr Arg Thr Pro Leu His Thr Ser Ala Gly Ile Ala Tyr Thr Asp
        35                  40                  45

Ser Cys Gly Ser Ile Arg Thr Glu Ser Thr Ile Tyr Gly Asp Ser Glu
    50                  55                  60

Met His Ile Tyr Phe Asn Gly Thr Glu Ser Lys Asp Glu Asn Arg Ser
65                  70                  75                  80

Val Lys Ser Val Leu Glu Arg Tyr Arg Asn Glu Leu Gln Ser Phe Phe
                85                  90                  95

Gly Lys Lys Asp Val Ser Tyr Ser Ser Leu Asn Tyr Gly Ile Leu Ser
            100                 105                 110

Gly Ser Ser Asp Ala Gly Ala Ala Ser Ile Gly Ala Ile Leu Ser Phe
        115                 120                 125

Ile Asp Lys Lys Asn Asp Ile His Asp Ile Glu Asn Asp Ile Arg Met
130                 135                 140

Ile Ser Glu Ser Ala Gly Arg Ser Leu His Gly Gly Leu Thr Ile Thr
145                 150                 155                 160

Trp Ser Asp Gly Tyr Ser Ala Tyr Thr Glu Arg Val Leu Gly Pro Glu
                165                 170                 175

His Phe Asn Asn Tyr Ala Ile Val Gly Phe Ser Phe Asp Tyr Pro Arg
            180                 185                 190

Asn Pro Ser Asp Thr Ile His Gln Asn Ile Ile Lys Ser Lys Arg Tyr
        195                 200                 205

Lys Gln Arg Thr Ile Asp Ala Asp Glu His Ala His Glu Ile Lys Glu
    210                 215                 220

Met Ala Arg Thr Asp Asp Ile Glu Gly Ile Phe Glu Lys Ala Glu Glu
225                 230                 235                 240

Asp Thr Glu Glu Tyr His Ser Ile Leu Arg Glu Val Gly Val Leu Val
                245                 250                 255

Ile Arg Glu Asn Met Gln Lys Leu Ile Glu Phe Ile Lys Ile Leu Arg
            260                 265                 270

Lys Glu Phe Trp Asn Ser Tyr Ile Val Thr Gly Gly Ser Asn Val Tyr
        275                 280                 285

Val Ile Val Arg Arg Asp Leu Glu Arg Leu Ile His Ile Lys Asn
    290                 295                 300

Thr Phe Gly Ser Lys Pro Lys Ile Leu Asn Val Ala Gly Pro Ala Trp
305                 310                 315                 320

Ile Lys Lys Val Glu Ser Asp
                325

<210> SEQ ID NO 18
<211> LENGTH: 325
<212> TYPE: PRT
```

<213> ORGANISM: Thermoplasma acidophilum

<400> SEQUENCE: 18

| | | | | | | | | | | | | | | | |
|---|---|---|---|---|---|---|---|---|---|---|---|---|---|---|---|
| Met | Leu | His | His | His | His | His | Thr | Tyr | Arg | Ser | Ile | Gly | Ser | Thr | |
| 1 | | | | 5 | | | | | 10 | | | | | 15 | |
| Ala | Tyr | Pro | Thr | Ile | Gly | Val | Val | Leu | Leu | Gly | Gly | Ile | Ala | Asn | Pro |
| | | | 20 | | | | | 25 | | | | | 30 | | |
| Val | Thr | Arg | Thr | Pro | Leu | His | Thr | Ser | Ala | Gly | Ile | Ala | Tyr | Ser | Asp |
| | | | 35 | | | | | 40 | | | | | 45 | | |
| Ser | Cys | Gly | Ser | Ile | Arg | Ser | Glu | Thr | Arg | Ile | Tyr | Ala | Asp | Glu | Ala |
| | 50 | | | | | 55 | | | | | 60 | | | | |
| Thr | His | Ile | Tyr | Phe | Asn | Gly | Thr | Glu | Ser | Thr | Asp | Asp | Asn | Arg | Ser |
| 65 | | | | | 70 | | | | | 75 | | | | | 80 |
| Val | Arg | Arg | Val | Leu | Asp | Arg | Tyr | Ser | Ser | Val | Phe | Glu | Glu | Ala | Phe |
| | | | | 85 | | | | | 90 | | | | | 95 | |
| Gly | Thr | Lys | Thr | Val | Ser | Tyr | Ser | Ser | Gln | Asn | Phe | Gly | Ile | Leu | Ser |
| | | | 100 | | | | | 105 | | | | | 110 | | |
| Gly | Ser | Ser | Asp | Ala | Gly | Ala | Ala | Ser | Ile | Gly | Ala | Ala | Ile | Leu | Gly |
| | | | 115 | | | | | 120 | | | | | 125 | | |
| Leu | Lys | Pro | Asp | Leu | Asp | Pro | His | Asp | Val | Glu | Asn | Asp | Leu | Arg | Ala |
| | 130 | | | | | 135 | | | | | 140 | | | | |
| Val | Ser | Glu | Ser | Ala | Gly | Arg | Ser | Leu | Phe | Gly | Gly | Leu | Thr | Ile | Thr |
| 145 | | | | | 150 | | | | | 155 | | | | | 160 |
| Trp | Ser | Asp | Gly | Phe | His | Ala | Tyr | Thr | Glu | Lys | Ile | Leu | Asp | Pro | Glu |
| | | | | 165 | | | | | 170 | | | | | 175 | |
| Ala | Phe | Ser | Gly | Tyr | Ser | Ile | Val | Ala | Phe | Ala | Phe | Asp | Tyr | Gln | Arg |
| | | | 180 | | | | | 185 | | | | | 190 | | |
| Asn | Pro | Ser | Asp | Val | Ile | His | Gln | Asn | Ile | Val | Arg | Ser | Asp | Leu | Tyr |
| | | | 195 | | | | | 200 | | | | | 205 | | |
| Pro | Ala | Arg | Lys | Lys | His | Ala | Asp | Glu | His | Ala | His | Met | Ile | Lys | Glu |
| | 210 | | | | | 215 | | | | | 220 | | | | |
| Tyr | Ala | Lys | Thr | Asn | Asp | Ile | Lys | Gly | Ile | Phe | Asp | Leu | Ala | Gln | Glu |
| 225 | | | | | 230 | | | | | 235 | | | | | 240 |
| Asp | Thr | Glu | Glu | Tyr | His | Ser | Ile | Leu | Arg | Gly | Val | Gly | Val | Asn | Val |
| | | | | 245 | | | | | 250 | | | | | 255 | |
| Ile | Arg | Glu | Asn | Met | Gln | Lys | Leu | Ile | Ser | Tyr | Leu | Lys | Leu | Ile | Arg |
| | | | 260 | | | | | 265 | | | | | 270 | | |
| Lys | Asp | Tyr | Trp | Asn | Ala | Tyr | Ile | Val | Thr | Gly | Gly | Ser | Asn | Val | Tyr |
| | | 275 | | | | | 280 | | | | | 285 | | | |
| Val | Ala | Val | Glu | Ser | Glu | Asn | Ala | Asp | Arg | Leu | Phe | Ser | Ile | Glu | Asn |
| | 290 | | | | | 295 | | | | | 300 | | | | |
| Thr | Phe | Gly | Ser | Lys | Lys | Lys | Met | Leu | Arg | Ile | Val | Gly | Gly | Ala | Trp |
| 305 | | | | | 310 | | | | | 315 | | | | | 320 |
| His | Arg | Arg | Pro | Glu | | | | | | | | | | | |
| | | | | 325 | | | | | | | | | | | |

<210> SEQ ID NO 19
<211> LENGTH: 329
<212> TYPE: PRT
<213> ORGANISM: Ferroplasma acidarmanus
<220> FEATURE:
<223> OTHER INFORMATION: fer1

<400> SEQUENCE: 19

| | | | | | | | | | | | | | | | |
|---|---|---|---|---|---|---|---|---|---|---|---|---|---|---|---|
| Met | His | His | His | His | His | His | Met | Glu | Lys | Tyr | Tyr | Val | Glu | Val | Lys |
| 1 | | | | 5 | | | | | 10 | | | | | 15 | |

```
Ala Tyr Pro Thr Ile Gly Ile Leu Leu Gly Gly Val Ser Asp Asn
         20                  25                  30

Lys Lys Arg Leu Pro Arg His Thr Ala Gly Ile Ala Tyr Thr Gly
     35                  40                  45

Leu Asp Asp Ile Tyr Val Lys Thr Asp Leu Tyr Leu Ser Asn Gln
 50                  55                  60

Lys Ser Gly Ile Ile Asn Gly Lys Glu Val Ser Pro Asp Ser Pro Arg
 65                  70                  75                  80

Ser Pro Phe Val Val Ile Asp Lys Tyr Arg His Glu Ile Leu Met Arg
                 85                  90                  95

His Pro Glu Tyr Ser Glu Val Ser Phe Val Ser Glu Asn Lys Asn Val
             100                 105                 110

Ile Ser Gly Ser Ser Asp Ala Gly Ala Ala Ile Gly Glu Cys Ile
             115                 120                 125

Gln Ser Ile Phe Glu Tyr Asn Ile Asn Ile Phe Asn Phe Glu Asn Asp
130                 135                 140

Leu Gln Gln Ile Ser Glu Ser Ala Gly Arg Ser Met Phe Gly Gly Phe
145                 150                 155                 160

Thr Ile Asn His Ala Asn Gly Lys Glu Ser Leu Thr Asp Glu Ile Leu
                 165                 170                 175

Gly Pro Glu Asp Phe Glu Asp Phe Val Ile Val Ala Cys Lys Phe Ser
             180                 185                 190

Glu Asp Arg Lys Pro Ser Asp Thr Ile His Ser Asn Ile Ile Asn His
             195                 200                 205

Glu Lys Tyr Ala Glu Arg Val Lys Asn Ser Glu Leu Arg Ala Lys Glu
210                 215                 220

Leu Glu Lys Met Ala Asp Ser Gly Asp Ile Lys Gly Ile Phe Glu Ala
225                 230                 235                 240

Gly Glu Lys Asp Thr Gln Glu Tyr His Ser Met Leu Arg Glu Val Gly
                 245                 250                 255

Val Ser Ile Ile Thr Asp Glu Met Gln Arg Leu Ile Glu Lys Val Glu
             260                 265                 270

Glu Leu Lys Ala Glu Phe Trp Asn Ala Tyr Ile Val Thr Gly Gly Thr
         275                 280                 285

Asn Val Phe Val Ala Val Glu Arg Lys Asn Met Glu Lys Met Lys Asn
     290                 295                 300

Ala Ala Met Glu Phe Lys Cys Thr Pro Val Tyr Leu Lys Val Ala Gly
305                 310                 315                 320

Lys Pro Asp Val Ile Ser Lys Asn Phe
                 325
```

<210> SEQ ID NO 20
<211> LENGTH: 993
<212> TYPE: DNA
<213> ORGANISM: Picrophilus torridus
<220> FEATURE:
<223> OTHER INFORMATION: (AAT43941) (including the His Tag)

<400> SEQUENCE: 20

```
atgcatcatc accatcacca tgaaaattac aatgttaaga caagggcgtt cccaacaata    60
ggcataatac tgcttggtgg gatctcggat aaaaagaaca ggataccgct gcatacaacg   120
gcaggcatag catatactgg tataaacaat gatgtttaca ctgagacaaa gctttatgta   180
tcaaaagatg aaaaatgcta tattgatgga aaggaaattg atttaaattc agatagatca   240
```

```
ccatcgaagg ttattgataa attcaagcat gaaatactta tgagagtaaa tcttgatgat      300
gaaaataacc tttcaattga ttcaaggaac tttaatatat taagtggcag ctcagattct      360
ggggccgctg cactgggaga gtgcatagaa tcaattttg aatacaatat aaatatattt      420
acatttgaaa acgatcttca gaggatatca gaaagtgttg gaagaagcct ttacggtggt      480
ttaacagtaa actatgccaa tggcagggaa tcattaacag agccattact tgagcctgag      540
gcatttaata actttacaat aattggtgca cattttaaca ttgatagaaa accatcaaat      600
gagattcatg aaaatatcat aaaacatgaa aattacaggg aaagaataaa aagtgctgag      660
agaaaggcga aaaacttga ggagctatca aggaatgcaa acataaaggg tatctttgaa      720
cttgcagaat ccgatacagt ggaataccat aaaatgctcc atgatgttgg cgttgacata      780
ataaatgata gaatggagaa cctcattgaa agggtaaaag aaatgaaaaa taacttctgg      840
aattcataca tagttaccgg cggcccgaac gttttttgtaa taacagagaa aaaggacgtt      900
gataaggcaa tggaaggatt aaatgatctg tgcgatgata taagattatt aaaagttgca      960
ggaaagccac aggtcatttc aaaaaacttt taa                                  993

<210> SEQ ID NO 21
<211> LENGTH: 996
<212> TYPE: DNA
<213> ORGANISM: Artificial Sequence
<220> FEATURE:
<223> OTHER INFORMATION: Description of Artificial Sequence: Codon
      optimized sequence of P. torridus (AAT43941) (including the
      His Tag)

<400> SEQUENCE: 21
atgcatcatc atcatcacca cgagaactat aatgttaaaa cccgtgcatt tccgaccatt       60
ggtattattc tgctgggtgg cattagcgac aaaaaaaacc gtattccgct gcataccacc      120
gcaggtattg catataccgg catcaataac gatgtgtaca ccgaaaccaa actgtatgtg      180
agcaaagacg aaaaatgcta tatcgatggc aaagaaatcg atctgaatag cgatcgtagc      240
ccgagcaaag tgatcgataa attcaaacat gaaatcctga tgcgtgtgaa tctggatgat      300
gaaaacaacc tgagcattga tagccgcaat tttaacattc tgagcggtag cagcgatagc      360
ggtgcagcag cactgggtga atgcattgaa agcatcttcg agtacaacat caacatcttc      420
acctttgaaa atgatctgca gcgtattagc gaaagcgttg gtcgtagcct gtatggtggt      480
ctgaccgtta attatgcaaa tggtcgtgaa agcctgaccg aaccgctgct ggaaccggaa      540
gcatttaaca actttaccat catcggtgcc cattttaaca ttgatcgcaa accgagcaac      600
gaaatccacg aaaacatcat caaacatgag aactatcgcg aacgtattaa aagcgcagag      660
cgcaaagcaa aaaaactgga agaactgagc cgtaatgcca acattaaagg cattttt gaa      720 ctggcagaaa gcgataccgt ggaatatcat aaaatgctgc atgatgtggg cgttgatatt      780
atcaatgacc gcatggaaaa tctgattgaa cgcgtgaaag atgaaaaaa caacttctgg      840 aacagctata ttgttaccgg tggtccgaat gttttttgtga tcaccgagaa aaaagatgtg      900
gataaagcca tggaaggtct gaatgatctg tgtgatgata ttcgtctgct gaaagttgca      960
ggtaaaccgc aggttatcag caaaaacttc taatga                                996
```

```
<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 22

His His His His His His
1               5
```

PROCESS FOR THE PRODUCTION OF ISOPRENOL FROM MEVALONATE EMPLOYING A DIPHOSPHO-MEVOLONATE DECARBOXYLASE

SEQUENCE LISTING

The instant application contains a Sequence Listing which has been submitted in ASCII format via EFS-Web and is hereby incorporated by reference in its entirety. Said ASCII copy, created on Aug. 23, 2012, is named 28622272.txt and is 59,418 bytes in size.

The present invention relates to a method for the production of isoprenol using mevalonate as a substrate and enzymatically converting it by a decarboxylation step into isoprenol. The present invention also relates to the use of an enzyme which is capable of catalyzing the decarboxylation of mevalonate for the production of isoprenol from mevalonate. Furthermore, it relates to the use of mevalonate as a starting material for the production of isoprenol in an enzymatically catalysed reaction.

Moreover, the present invention relates to a method for the production of isoprene comprising the method for the production of isoprenol using mevalonate as a substrate and enzymatically converting it by a decarboxylation step into isoprenol and further comprising the step of converting the produced isoprenol into isoprene. The present invention also relates to a method for the production of isoamyl alcohol comprising the method for the production of isoprenol using mevalonate as a substrate and enzymatically converting it by a decarboxylation step into isoprenol and further comprising the step of converting the produced isoprenol into isoamyl alcohol.

Isoprenol responds to the formula $C_5H_{10}O$. It can be used to produce prenol which is used in perfumes or as a building block in the pharmaceutical industry. It is produced by the chemical condensation of isobutene and formaldehyde, leading to isoprenol further isomerised into prenol.

The route which is presently used to produce isoprenol involves the mevalonate pathway: mevalonate is produced, then diphoshorylated, then decarboxylated-dehydrated into isoprenyl-pyrophosphat, and finally dephosphorylated twice into isoprenol (US patent application 20080092829).

Isoprenol can be converted into isoprene which is a key compound for the tire industry, and also has many applications in the adhesives. It is produced chemically using several routes:

Extractive distillation from oil (C5 cut)
Dehydrogenation of iso-amylene
Double dehydrogenation of isopentane
Reaction of isobutene and formaldehyde
Reaction of acetone and acetylene
Propylene dimerization WO 2009/076676 reports a metabolic pathway to isoprene. The pathway is based on the dephosphorylation-dehydration of downstream intermediates in the mevalonate pathway, i.e. isoprenyl-pyrophosphate or prenyl-pyrophosphate. This process has the drawback of requiring to go through the whole mevalonate pathway: double phosphorylation of mevalonate, followed by a decarboxylation-dehydration into isoprenyl-pyrophosphate, further isomerised into prenyl-pyrophosphate, and finally double dephosphorylation/dehydration into isoprene.

Isoamyl alcohol is a very important chemical commonly used as solvents for fats, oils, resins and alkaloids. There is a demand for isoamyl alcohol in perfumery industry, for example in the manufacture of isoamyl salicylate used in soap and cosmetic fragrances. It is also used in the manufacture of phosphoric acid. Furthermore, it is used in the synthesis of pyrethroids. Commercial processes for the production of isoamyl alcohol include fractionation of fusel oils, chlorination of alkanes with subsequent hydrolysis to produce a mixture of isomers and a low pressure oxo-process or hydroformylation of n-butenes followed by hydrogenation of the resulting iso-valeraldehyde.

There is a need to provide environmentally friendly, cost efficient and simple methods for producing the above-mentioned compounds. This need is met by the subject matter as recited in the claims.

Thus, in a first aspect, the present invention relates to a method for producing isoprenol from mevalonate. In particular, the present invention relates to a method for producing isoprenol from mevalonate which is characterized by a conversion of mevalonate with an enzyme having a decarboxylase activity. Thus, the method comprises the enzymatically catalyzed decarboxylation of mevalonate. The term "decarboxylation" when used in the context of the present invention preferably refers to a dehydrative decarboxylation.

The term "mevalonate" comprises mevalonic acid as well as the anion of mevalonic acid which is the predominant form in biological media. Mevalonic acid is a precursor in the biosynthetic pathway, known as the mevalonate pathway that produces terpenes and steroids. Mevalonate is the primary precursor of isoprenyl pyrophosphate that is in turn the basis for all terpenoids. The structural formula of mevalonic acid is shown in FIG. 1.

In the context of the present invention the term isoprenol comprises compounds which respond to the formula $C_5H_{10}O$. The IUPAC name of isoprenol is 3-methylbut-3-en-1-ol. Synonyms of isoprenol are, for example, 2-methyl-1-buten-4-ol, 3-buten-1-ol-3-methyl, 3-isopentenyl alcohol, 3-methyl-3-buten-1-ol, isobutenylcarbinol, isopropenylethyl alcohol and methallyl carbinol.

Figure 2:
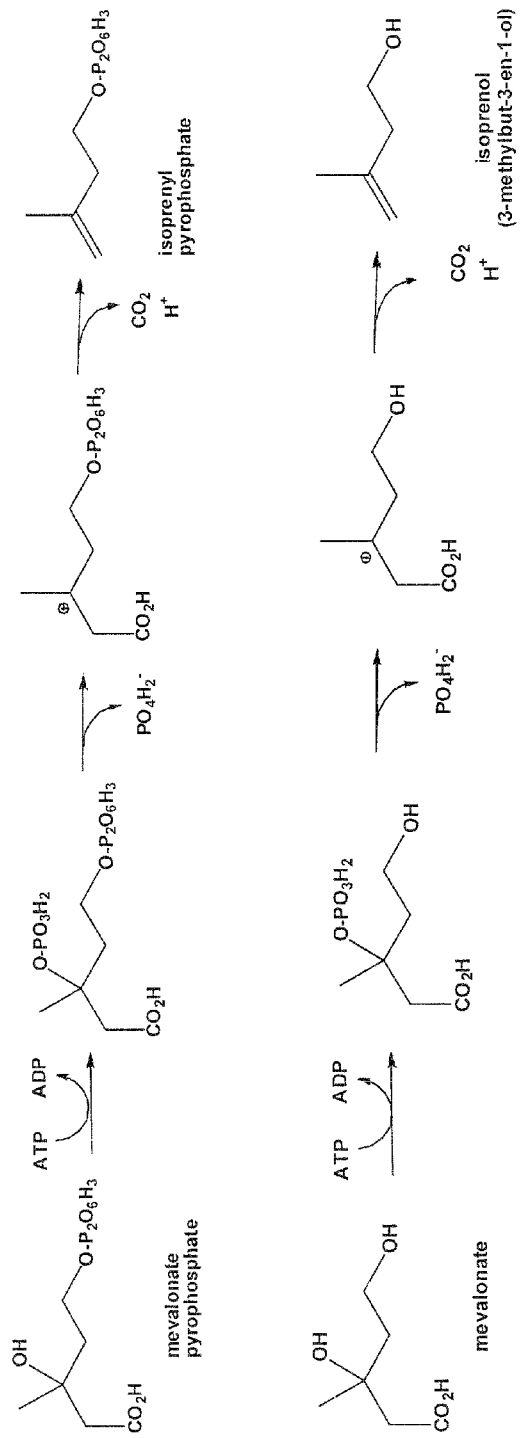

The term "enzyme having a decarboxylase activity" in the context of the present invention refers to an enzyme which is capable of decarboxylating mevalonate, in particular according to the reaction scheme given in FIG. 2. The catalyzed reaction is a simultaneous dehydration and decarboxylation. This enzymatic activity can be measured as described in the appended Examples 1 or 7.

In a preferred embodiment the enzyme having the activity of a decarboxylase is an enzyme which is classified as a diphosphomevalonate decarboxylase or is an enzyme which is derived from such an enzyme and which has the capacity to decarboxylate mevalonate so as to produce isoprenol. Diphosphomevalonate decarboxylase is classified with the EC number EC 4.1.1.33. A diphosphomevalonate decarboxylase is able to catalyze the decarboxylation of mevalonate diphosphate. In this reaction ATP and 5-diphosphomevalonate are converted into ADP, phosphate, isoprenyl pyrophosphate and $CO_2$. The reaction catalyzed by a diphosphomevalonate decarboxylase is shown in FIG. 2. The activity of a diphosphomevalonate decarboxylase can be measured according to methods known in the art, e.g. in Reardon et al. (Biochemistry 26 (1987), 4717-4722). Preferably, the activity is measured as described in Example 1 or 7 wherein diphosphomevalonate is used instead of mevalonate.

It has been reported that at least in some cases the reaction is divalent cation-dependent (see, e.g., Krepkiy et al., Protein Science 13 (2004), 1875-1881; Michihara et al., Biol. Pharm. Bull. 25 (2002), 302-306).

Diphosphomevalonate decarboxylase is an enzyme which, in its natural function, is part of the mevalonate pathway for isoprenoid synthesis in bacteria and of the sterol biosynthesis pathway in eukaryotes. It has been identified and isolated from various organisms such as animals, fungi, yeasts and bacteria. It is also expressed by certain plants.

The three-dimensional structure of several diphosphomevalonate decarboxylases has already been determined (see, e.g., Byres et al. (J. Mol. Biol. 371 (2007), 540-553); Bonanno et al. (Proc. Natl Acad. Sci. USA 98 (2001), 12896-12901); Voynova et al., Archives of Biochemistry and Biophysics 480 (2008), 58-67)) and considerable knowledge is available about its active site, amino acid residues crucial for the catalytic reaction and the actual enzymatic reaction (see, e.g. Byres et al. (J. Mol. Biol. 371 (2007), 540-553); Bonanno et al. (Proc. Natl Acad. Sci. USA 98 (2001), 12896-12901)). In most cases the enzyme is composed of about 300 to 400 amino acids and uses ATP as cosubstrate which is converted during the decarboxylation reaction into ADP and inorganic phosphate.

Diphosphomevalonate decarboxylases have been described for various organisms and also amino acid and nucleotide sequences encoding them are available for numerous sources.

In principle any diphosphomevalonate decarboxylase can be used in the context of the present invention, in particular from prokaryotic or eukaryotic organisms. Eukaryotic diphosphomevalonate decarboxylases are described, for example, for animals such as *Rattus norvegicus, Gallus gallus, Homo sapiens, Mus musculus, Sus scrofa, D. melanogaster, C. elegans* and *Trypanosoma brucei*, for plants such as *Arabidopsis thaliana, Ginko biloba, Oryza sativa, Pisum sativum*, for yeasts, such as *Saccharomyces cerevisiae* and *Candida albicans*. Also numerous prokaryotic diphosphomevalonate decarboxylases have been described, e.g. for *Helicobacter, Staphylococcus aureus, Streptococcus pneumoniae, Enterococcus faecium, Listeria monocytgenes, Leuconostoc citreum, Lactobacillus reuteri*, to name just some. Table 1 provides a list of sequences of diphosphomevalonate decarboxylases from different organisms indicating the accession numbers under which they can be retrieved from the respective databases.

TABLE 1

| Organism | Genebank Accession number |
| --- | --- |
| *Bombyx mori* | A5A7A2 |
| *Saccharomyces cerevisiae* strain YJM7 | A6ZSB7 |
| *Solanum lycopersicum* | A8WBX7 |
| *Hevea brasiliensis* | A9ZN03 |
| *Nicotiana langsdorffii* x *Nicotiana sanderae* | B3F8H5 |
| *Saccharomyces cerevisiae* (strain RM11-1a) | B3LPK0 |
| *Phaeodactylum tricornutum* CCAP 1055 | B7S422 |
| *Candida dubliniensis* | B9W6G7 |
| *Pichia pastoris* | C4QX63 |
| *Ashbya gossypii* | Q751D8 |
| *Bos taurus* | Q0P570 |
| *Danio rerio* | Q5U403 |
| *Debaryomyces hanseni* | Q6BY07 |
| *Dictyostelium discoideum* | Q54YQ9 |
| *Homo sapiens* | P53602 |
| *Mus musculus* | Q99JF5 |
| *Rattus norvegicus* | Q62967 |
| *Schizosaccharomyces pombe* | O13963 |
| *Saccharomyces cerevisiae* | P32377 |
| *Arnebia euchroma* | Q09RL4 |
| *Aspergillus oryzae* | Q2UGF4 |
| *Mus musculus* | Q3UYC1 |
| *Ginkgo biloba* | Q5UCT8 |
| *Rattus norvegicus* | Q642E5 |

TABLE 1-continued

| Organism | Genebank Accession number |
| --- | --- |
| *Oryza sativa* subsp. *japonica* | Q6ETS8 |
| *Arabidopsis thaliana* | Q8LB37 |
| *Encephalitozoon cuniculi* | Q8SRR7 |
| *Hevea brasiliensis* | Q944G0 |

Examples of diphosphomevalonate decarboxylases from different organisms are given in SEQ ID NO: 1 to 19. In a preferred embodiment of the present invention the diphosphomevalonate decarboxylase is an enzyme comprising an amino acid sequence selected from the group consisting of SEQ ID NO: 1 to 19 or a sequence which is at least n % identical to any of SEQ ID NO: 1 to 19 and having the activity of a diphosphomevalonate decarboxylase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99.

Preferably, the degree of identity is determined by comparing the respective sequence with the amino acid sequence of any one of the above-mentioned SEQ ID NOs. When the sequences which are compared do not have the same length, the degree of identity preferably either refers to the percentage of amino acid residues in the shorter sequence which are identical to amino acid residues in the longer sequence or to the percentage of amino acid residues in the longer sequence which are identical to amino acid residues in the shorter sequence. The degree of sequence identity can be determined according to methods well known in the art using preferably suitable computer algorithms such as CLUSTAL.

When using the Clustal analysis method to determine whether a particular sequence is, for instance, 80% identical to a reference sequence default settings may be used or the settings are preferably as follows: Matrix: blosum 30; Open gap penalty: 10.0; Extend gap penalty: 0.05; Delay divergent: 40; Gap separation distance: 8 for comparisons of amino acid sequences. For nucleotide sequence comparisons, the Extend gap penalty is preferably set to 5.0.

Preferably, the degree of identity is calculated over the complete length of the sequence.

Moreover, if the term "homology" is used in the context of the present invention, this term preferably means "sequence identity".

In a preferred embodiment the decarboxylase employed in the method according to the invention is a diphosphomevalonate decarboxylase from *Picrophilus torridus* or an organism which is evolutionary closely related to *Picrophilus torridus*. In a further preferred embodiment the decarboxylase originates from an organism of the genus *Picrophilus, Thermoplasma* or *Ferroplasma*, more preferably of the species *Picrophilus torridus, Picrophilus oshimae, Thermoplasma volcanicum, Thermoplasma acidophilum, Ferroplasma acidarmanus* or *Ferroplasma cupricumulans*.

In a particularly preferred embodiment the decarboxylase employed in the method according to the invention is a diphosphomevalonate decarboxylase which comprises the amino acid sequence as depicted in SEQ ID NO: 6, 16, 17, 18 or 19 or which comprises an amino acid sequence which is at least n % identical to any of SEQ ID NO: 6, 16, 17, 18 or 19 and which has the activity of a diphosphomevalonate decarboxylase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. The enzyme showing the amino acid sequence as shown in SEQ ID NOs:6 and 16 originates from *Picrophilus torridus*. As shown in the Examples, this enzyme is particularly efficient in catalyzing the decarboxylation of mevalonate to isoprenol. Further preferred decarboxylases to be employed in the method according to the present invention are diphosphomevalonate decarboxylases which originate from organisms which are phylogenetically closely related to *Picrophilus torridus*, such as other bacteria of the genus *Picrophilus*, such as *Picrophilus oshimae*, bacteria of the genus *Ferroplasma*, e.g. *Ferroplasma acidarmanus* (SEQ ID NO:19), or of the genus *Thermoplasma*, such as *Thermoplasma acidophilum* (SEQ ID NO:18) and *Thermoplasma volcanium* (SEQ ID NO:17). The diphosphomevalonate decarboxylase of *Thermoplasma acidophilum* (AC number Q9HIN1) shows a homology of 38% to SEQ ID NO:6 and that of *Thermoplasma volcanium* (AC number Q97BY2) shows a homology of about 42% to SEQ ID NO:6.

In a further particularly preferred embodiment the decarboxylase employed in the method according to the invention is a diphosphomevalonate decarboxylase which is encoded by a nucleotide sequence as shown in SEQ ID NO: 20 or 21 or by a nucleotide sequence which is at least n % identical to any of SEQ ID NO: 20 or 21 and which encodes an enzyme having the activity of a diphosphomevalonate decarboxylase with n being an integer between 10 and 100, preferably 10, 15, 20, 25, 30, 35, 40, 45, 50, 55, 60, 65, 70, 75, 80, 85, 90, 91, 92, 93, 94, 95, 96, 97, 98 or 99. SEQ ID NO: 20 is the native nucleotide sequence encoding the MDP decarboxylase from *P. torridus* including at the N-terminus a His-tag. SEQ ID NO: 21 is a codon optimized sequence coding for the MDP decarboxylase from *P. torridus* including at the N-terminus a His-tag.

The decarboxylase, preferably diphosphomevalonate decarboxylase, employed in the process according to the invention can be a naturally occurring decarboxylase, preferably diphosphomevalonate decarboxylase, or it can be a decarboxylase, preferably diphosphomevalonate decarboxylase, which is derived from a naturally occurring decarboxylase, preferably diphosphomevalonate decarboxylase, e.g. by the introduction of mutations or other alterations which, e.g., alter or improve the enzymatic activity, the stability, etc.

The term "decarboxylase", "diphosphomevalonate decarboxylase", "a protein/enzyme having the activity of a decarboxylase" or "a protein/enzyme having the activity of a diphosphomevalonate decarboxylase" in the context of the present application also covers enzymes which are derived from a decarboxylase, preferably a diphosphomevalonate decarboxylase, which are capable of catalyzing the decarboxylation of mevalonate but which only have a low affinity to their natural substrate, e.g. mevalonate diphosphate, or do no longer accept their natural substrate, e.g. mevalonate diphosphate. Such a modification of the preferred substrate, in particular of a diphosphomevalonate decarboxylase, allows to improve the conversion of mevalonate into isoprenol and to reduce the production of the possibly occurring by-product isoprenyl pyrophosphate. Methods for modifying and/or improving the desired enzymatic activities of proteins are well-known to the person skilled in the art and include, e.g., random mutagenesis or site-directed mutagenesis and subsequent selection of enzymes having the desired properties or approaches of the so-called "directed evolution", DNA shuffling or in vivo evolution.

For example, for genetic engineering in prokaryotic cells, a nucleic acid molecule encoding a decarboxylase, preferably a diphosphomevalonate decarboxylase, can be introduced into plasmids which permit mutagenesis or sequence modification by recombination of DNA sequences. Standard methods (see Sambrook and Russell (2001), Molecular Cloning: A Laboratory Manual, CSH Press, Cold Spring Harbor, N.Y., USA) allow base exchanges to be performed or natural or synthetic sequences to be added. DNA fragments can be connected to each other by applying adapters and linkers to the fragments. Moreover, engineering measures which provide suitable restriction sites or remove surplus DNA or restriction sites can be used. In those cases, in which insertions, deletions or substitutions are possible, in vitro mutagenesis, "primer repair", restriction or ligation can be used. In general, a sequence analysis, restriction analysis and other methods of biochemistry and molecular biology are carried out as analysis methods. The resulting decarboxylase, preferably diphosphomevalonate decarboxylase, variants are then tested for their enzymatic activity and in particular for their capacity to prefer mevalonate as a substrate rather than, e.g. mevalonate diphosphate.

Such methods for identifying variants with improved enzymatic properties as regards the production of isoprenol may also be carried out in the presence of a cofactor which allows for a steric and/or electronic complementation in the catalytic site of the enzyme due to the fact that the substrate mevalonate is shorter than the natural substrate, e.g. mevalonate diphosphate in the case of diphosphomevalonate decarboxylase. Examples for such a cofactor would be phosphono-phosphate or phosphonamido-phosphate (see FIG. 7) or orthophosphate.

The modified version of the decarboxylase, preferably diphosphomevalonate decarboxylase, accepting or preferring mevalonate as a substrate but having a low affinity to its natural product, e.g. mevalonate diphosphate, as a substrate or no longer accepting its natural product, e.g. mevalonate diphosphate, as a substrate may be derived from a naturally occurring decarboxylase, preferably diphosphomevalonate decarboxylase, or from an already modified, optimized or synthetically synthesized decarboxylase, preferably diphosphomevalonate decarboxylase.

It has surprisingly been found that diphosphomevalonate decarboxylase is not only capable of catalyzing the decarboxylation of mevalonate diphosphate but can also accept mevalonate as a substrate and can decarboxylate it despite the absence of the diphosphate group. This is in particular surprising since Jabalquinto and Cardemil (Biochim. Biophys. Acta 996 (1989), 257-259), who investigated the substrate binding requirements of diphosphomevalonate decarboxylase, pointed out the importance of the diphosphoric moiety of mevalonate diphosphate to the binding of this substrate to the catalytic site of the enzyme (see page 259). In this context, it is important to note the substantial differences between mevalonate and diphosphomevalonate. Mevalonte only has a molecular weight of about 148 Da while diphosphomevalonate has a molecular weight of 308 Da and the phosphate groups are carrying three additional charges.

The decarboxylase, preferably diphosphomevalonate decarboxylase, employed in the process according to the present invention can be a natural version of the protein or a synthetic protein as well as a protein which has been chemically synthesized or produced in a biological system or by recombinant processes. The decarboxylase, preferably diphosphomevalonate decarboxylase, may also be chemically modified, for example in order to improve its/their stability, resistance, e.g. to temperature, for facilitating its/their purification or its immobilization on a support. The decarboxylase, preferably diphosphomevalonate decarboxylase, may be used in isolated form, purified form, in immobilized form, as a crude or partially purified extract obtained from cells synthesizing the enzyme, as chemically synthesized enzyme, as recombinantly produced enzyme, in the form of organism/microorganisms producing them etc.

The method according to the present invention may be carried out in vitro or in vivo. An in vitro reaction is understood to be a reaction in which no cells are employed, i.e. an acellular reaction.

For carrying out the process in vitro the substrates for the reaction and the enzyme are incubated under conditions (buffer, temperature, cosubstrates, cofactors etc.) allowing the enzyme to be active and the enzymatic conversion to occur. The reaction is allowed to proceed for a time sufficient to produce isoprenol. The production of isoprenol can be measured by methods known in the art, such as chromatography. e.g. thin layer chromatography or liquid or gas chromatography possibly linked to mass spectrometry detection.

The enzyme may be in any suitable form allowing the enzymatic reaction to take place. It may be purified or partially purified or in the form of crude cellular extracts or partially purified extracts. It is also possible that the enzyme is immobilized on a suitable carrier.

If required, a co-substrate, a co-factor or ions are also added. It is described, for example, that some diphosphomevalonate decarboxylase enzymes use ATP as a co-substrate which is converted into ADP and inorganic phosphate during the decarboxylation reaction. Thus, in a preferred embodiment, ATP is added to the reaction when carrying out the method according to the invention. However, instead of ATP any other suitable rNTP (ribonucleoside triphosphate) or dNTP (desoxyribonucleoside triphosphate) or any mixture of these can be added to the reaction mixture. Also possible is the addition of pyrophosphate or another polyphosphate or a molecule containing a phosphoanhydride group (POP). Moreover, any mixture of any of the afore-mentioned compounds can be added. Moreover, it is described for some diphosphomevalonate decarboxylase enzymes that they require divalent cations. Thus, in a preferred embodiment, and if necessary, a suitable amount of a suitable divalent cation is added to the reaction when carrying out the method according to the invention. The divalent cation is preferably $Mg^{2+}$, $Mn^{2+}$ or $Co^{2+}$, but it is possible to also use other divalent cations such as $Ca^{2+}$. Of course, the nature of the divalent cation depends on the need of the diphosphomevalonate decarboxylase enzyme in question.

Since the substrate mevalonate is in general shorter than the natural substrate used by the enzyme, e.g. mevalonate diphosphate used by diphosphomevalonate decarboxylase, it may be advantageous to add to the reaction mixture a cofactor which allows for a steric and/or electronic complementation in the catalytic site of the enzyme. Examples for such a cofactor, in the case of diphosphomevalonate decarboxylase, would be phosphono-phosphate or phosphonamido-phosphate (see FIG. 7) or orthophosphate.

For carrying out the process in vivo use is made of a suitable organism/microorganism(s) which is/are capable of providing the substrates, i.e. mevalonate, and an enzyme which is capable of catalyzing the decarboxylation of mevalonate into isoprenol. In a preferred embodiment said enzyme is a diphosphomevalonate decarboxylase. There are two alternate pathways that lead to isoprenyl-pyrophosphate. One is the mevalonate pathway, observed in eukaryotes and some prokaryotes, especially in the firmicute phylum. All these organisms thus produce mevalonate. Most of the bacteria, including *E. coli*, use the other pathway (DXP pathway) and are thus not producing mevalonate. However, the latter can be genetically modified so as to produce mevalonate. For example, the implementation of the mevalonate pathway in *E. coli* has already been done successfuly (Maury et al., FEBS Lett. 582 (2008), 4032). Overexpression of only the upstream part (thiolase, HMG-CoA synthase, HMG-CoA reductase) in organisms that have or that do not have the mevalonate pathway allows for the production of high levels of mevalonate.

In a preferred embodiment, the organism employed in the method according to the invention is an organism, preferably a microorganism, which has been genetically modified to contain a foreign nucleic acid molecule encoding an enzyme which is capable of catalyzing the decarboxylation of mevalonate to isoprenol. In a preferred embodiment the organism has been genetically modified so as to contain a foreign nucleic acid molecule encoding diphosphomevalonate decarboxylase. The term "foreign" in this context means that the nucleic acid molecule does not naturally occur in said organism/microorganism. This means that it does not occur in the same structure or at the same location in the organism/microorganism. In one preferred embodiment, the foreign nucleic acid molecule is a recombinant molecule comprising a promoter and a coding sequence encoding the respective enzyme, e.g. a diphosphomevalonate decarboxylase, in which the promoter driving expression of the coding sequence is heterologous with respect to the coding sequence. Heterologous in this context means that the promoter is not the promoter naturally driving the expression of said coding sequence but is a promoter naturally driving expression of a different coding sequence, i.e., it is derived from another gene, or is a synthetic promoter or a chimeric promoter. Preferably, the promoter is a promoter heterologous to the organism/microorganism, i.e. a promoter which does naturally not occur in the respective organism/microorganism. Even more preferably, the promoter is an inducible promoter. Promoters for driving expression in different types of organisms, in particular in microorganisms, are well known to the person skilled in the art.

In another preferred embodiment the nucleic acid molecule is foreign to the organism/microorganism in that the encoded enzyme, e.g. the diphosphomevalonate decarboxylase, is not endogenous to the organism/microorganism, i.e. are naturally not expressed by the organism/microorganism when it is not genetically modified. In other words, the encoded decarboxylase, e.g. diphosphomevalonate decarboxylase, is heterologous with respect to the organism/microorganism.

The foreign nucleic acid molecule may be present in the organism/microorganism in extrachromosomal form, e.g. as plasmid, or stably integrated in the chromosome. A stable integration is preferred.

In a further preferred embodiment the organism/microorganism is characterized in that the expression/activity of an enzyme which is capable of catalyzing the decarboxylation of mevalonate to isoprenol, preferably a diphosphomevalonate decarboxylase, is higher in the organism/microorganism genetically modified with the foreign nucleic acid molecule in comparison to the corresponding non-genetically modified organism/microorganism. A "higher" expression/activity means that the expression/activity of the enzyme, preferably the diphosphomevalonate decarboxylase, in the genetically modified microorganism is at least 10%, preferably at least 20%, more preferably at least 30% or 50%, even more preferably at least 70% or 80% and particularly preferred at least 90% or 100% higher than in the corresponding non-genetically modified organism/microorganism. In even more preferred embodiments the increase in expression/activity may be at least 150%, at least 200% or at least 500%.

The term "higher" expression/activity also covers the situation in which the corresponding non-genetically modified organism/microorganism does not express a corresponding enzyme, e.g. a diphosphomevalonate decarboxylase, so that the corresponding expression/activity in the non-genetically modified organism/microorganism is zero.

Methods for measuring the level of expression of a given protein in a cell are well known to the person skilled in the art. In one embodiment, the measurement of the level of expression is done by measuring the amount of the corresponding protein. Corresponding methods are well known to the person skilled in the art and include Western Blot, ELISA etc. In another embodiment the measurement of the level of expression is done by measuring the amount of the corresponding RNA. Corresponding methods are well known to the person skilled in the art and include, e.g., Northern Blot.

Methods for measuring the enzymatic activity of the above-mentioned enzymes, in particular diphosphomevalonate decarboxylase, are known in the art and have already been described above.

The term "organism" as used in the context of the present invention refers in general to any possible type of organism, in particular eukaryotic organisms, bacterial organisms and archae. The term includes animal, plants, fungi, bacteria and archae. The term also includes isolated cells or cell aggregates of such organisms, like tissue or calli.

In one preferred embodiment, the organism is a microorganism. The term "microorganism" in the context of the present invention refers to prokaryotic cells, in particular bacteria, as well as to fungi, such as yeasts, and also to algae and archaebacteria. In one preferred embodiment, the microorganism is a bacterium. In principle any bacterium can be used. Preferred bacteria to be employed in the process according to the invention are all classical production strains for which the engineering tools have been developed. In a particularly preferred embodiment the bacterium belongs to the genus *Escherichia* or *Bacillus* and even more preferred to the species *Escherichia coli* or to the species *Bacillus subtilis*.

In another preferred embodiment the microorganism is a fungus. Preferred fungi to be employed in the process according to the invention are all classical production strains for which the engineering tools have been developed. More preferably the fungus is a yeast, preferably of the genus *Saccharomyces, Schizosaccharomyces, Pichia* or *Kluyveromyces* and even more preferably of the species *Saccharomyces cerevisia, Schizosaccharomyces pombe, Pichia pastoris* or of the species *Kluyveromyces lactis*. Other preferred fungi are those of the genus *Trichoderma* or *Aspergillus*, more preferably of the species *Trichoderma reesei* or *Aspergillus niger*.

In still another preferred embodiment the microorganism is a photosynthetically active microorganism such as bacteria which are capable of carrying out photosynthesis or microalgae.

In a particularly preferred embodiment the microorganism is an algae, more preferably an algae belonging to the diatomeae.

When the process according to the invention is carried out in vivo by using an organism/microorganism providing the respective enzyme activity, the organism, preferably microorganism, is cultivated under suitable culture conditions allowing the occurrence of the enzymatic reaction. The specific culture conditions depend on the specific organism/microorganism employed but are well known to the person skilled in the art. The culture conditions are generally chosen in such a manner that they allow the expression of the genes encoding the enzymes for the respective reaction. Various methods are known to the person skilled in the art in order to improve and fine-tune the expression of certain genes at certain stages of the culture such as induction of gene expression by chemical inducers or by a temperature shift.

In another preferred embodiment the organism employed in the method according to the invention is a plant. In principle any possible plant can be used, i.e. a monocotyledonous plant or a dicotyledonous plant. It is preferable to use a plant which can be cultivated on an agriculturally meaningful scale and which allows to produce large amounts of biomass. Examples are grasses like *Lolium*, cereals like rye, wheat, barley, oat, millet, maize, other starch storing plants like potato or sugar storing plants like sugar cane or sugar beet. Conceivable is also the use of tobacco or of vegetable plants such as tomato, pepper, cucumber, egg plant etc. Another possibility is the use of oil storing plants such as rape seed, olives etc. Also conceivable is the use of trees, in particular fast growing trees such as *eucalyptus*, poplar or rubber tree (*Hevea brasiliensis*).

The present invention also relates to the use of an organism, preferably a microorganism, which expresses an enzyme which is capable of catalyzing the decarboxylation of mevalonate, preferably an enzyme with the activity of a diphosphomevalonate decarboxylase, for the production isoprenol by the decarboxylation of mevalonate.

I.e., the present invention also relates to the use of an organism/microorganism as described in the context of the method according to the invention for the production of isoprenol.

Moreover, the present invention also relates to a composition comprising (i) mevalonate; and (ii) an enzyme which is capable of catalyzing the decarboxylation of mevalonate.

For the preferred embodiments of the enzyme the same applies as has already been set forth above in connection with the method according to the invention.

In a particularly preferred embodiment, the composition also comprises a co-substrate (such as ATP), a co-factor and/or divalent cations (such as $Mn^{2+}$, $Mg^{2+}$, $Co^{2+}$ or $Ca^{2+}$).

Moreover, the present invention also relates to the use of an enzyme which is capable of catalyzing the decarboxylation of mevalonate, preferably a diphosphomevalonate decarboxylase, for the production of isoprenol.

For the preferred embodiments of the enzyme the same applies as has already been set forth above in connection with the method according to the invention.

The present invention also relates to the use of mevalonate for the production of isoprenol, in particular by the enzymatic conversion of mevalonate to isoprenol by a decarboxylation step. In a preferred embodiment the enzymatic conversion is achieved by an enzyme as described above in connection with the method according to the invention, more preferably with an enzyme having the enzymatic activity of a diphosphomevalonate decarboxylase, and most preferably the conversion is achieved by the use of an organism as described in the context of the method according to the invention.

In addition the present invention also relates to a method for producing isoprene from mevalonate comprising the method for producing isoprenol according to the invention as described above and further comprising the step of converting the produced isoprenol into isoprene. The conversion of isoprenol into isoprene can be achieved by means and methods known to the person skilled in the art. In particular, the respective reaction is a dehydration reaction.

Moreover, the present invention also relates to a method for producing isoamyl alcohol from mevalonate comprising the method for producing isoprenol according to the invention as described above and further comprising the step of converting the produced isoprenol into isoamyl alcohol. The conversion of isoprenol into isoamyl alcohol can be achieved by means and methods known to the person skilled in the art. In particular, the respective reaction is a hydrogenation reaction.

FIG. 1: shows the chemical structure of mevalonate

Figure 3:
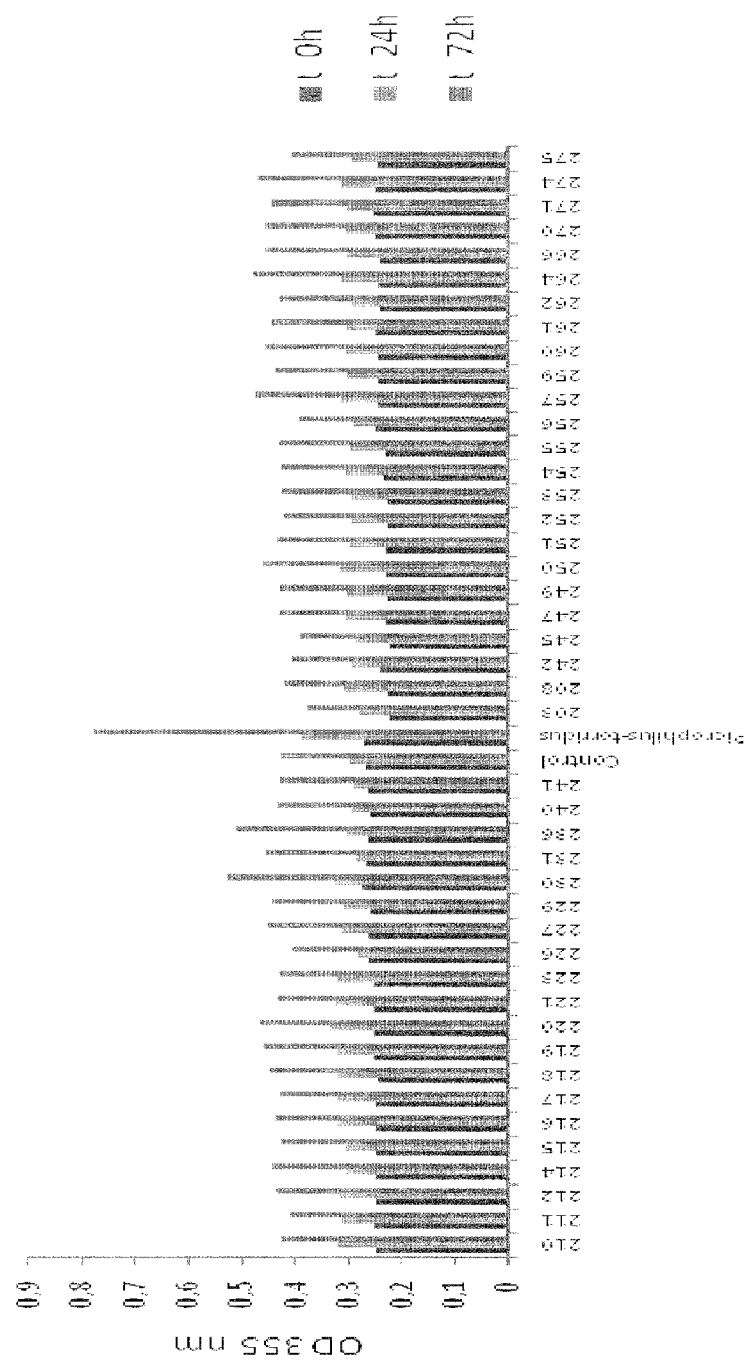

FIG. 2: shows the reaction of diphosphomevalonate decarboxylase on the physiological substrate diphosphomevalonate and on the precursor mevalonate FIG. 3: shows an example of screening of enzyme library for mevalonate decarboxylase activity by following inorganic phosphate production. The control reaction was carried out with extract of *E. coli* BL21(DE3) transformed with pET 22b lacking MDP decarboxylase gene.

FIG. 4: (a) shows the results of optimisation of *P. torridus* MDP decarboxylase expression in *E. coli*. SDS-PAGE analysis of samples of proteins obtained from the expression of native *P. torridus* MDP decarboxylase DNA sequence (lanes 1 to 3) and of optimized gene (lanes 4 to 6). (b) shows Mevalonate decarboxylation activity of crude lysate of *E. coli* obtained from the expression of native *P. torridus* MDP decarboxylase DNA sequence and of optimized gene. Control reaction was carried out with extract of *E. coli* BL21 (DE3) transformed with pET 22b lacking MDP decarboxylase gene. The enzyme activity was detected via inorganic phosphate production measurement.

Figure 5:
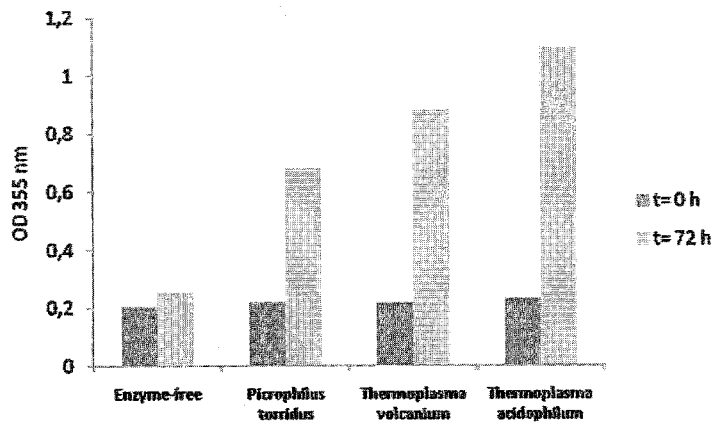

FIG. 5: shows the comparison of mevalonate decarboxylation activity among MDP decarboxylases from the *Picrophilus/Thermoplasma* phylum. The enzyme activity was detected by means of inorganic phosphate production measurement.

Figure 6:
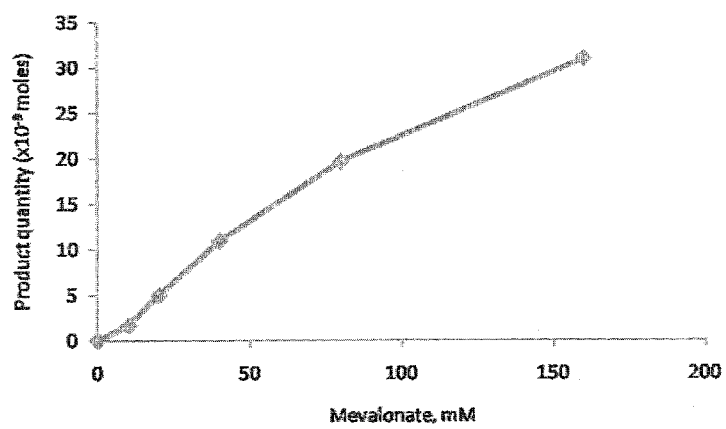

FIG. 6: shows product formation as function of mevalonate concentration. The product formation was followed by permanganate assay.

Figure 7:
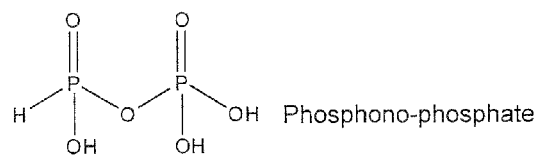
Figure 7:
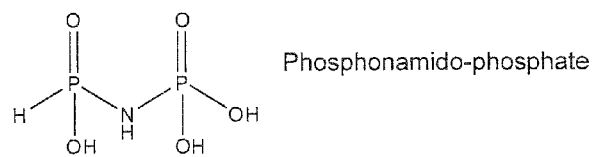

FIG. 7: shows the structure of phosphono-phosphate and phosphonamido-phosphate.

The following Examples serve to illustrate the invention.

EXAMPLE 1

Screening of a Library of MDP Decarboxylase for Mevalonate Decarboxylation Activity A library of 63 genes encoding enzymes of the MDP decarboxylase family was constructed and tested for activity on mevalonate as substrate.

Cloning, Bacterial Cultures and Expression of Proteins

The genes encoding mevalonate diphosphate (MDP) decarboxylase EC 4.1.1.33 were cloned in the pET 25b vector (Novagen) in the case of eukaryotic genes and in pET 22b (Novagen) in the case of prokaryotic genes. A stretch of 6 histidine codons ("6 histidine" disclosed as SEQ ID NO: 22) was inserted after the methionine initiation codon to provide an affinity tag for purification. Competent *E. coli* BL21(DE3) cells (Novagen) were transformed with these vectors according to the heat shock procedure. The transformed cells were grown with shaking (160 rpm) at 30° C. in terrific broth (TB) medium containing 0.5 M sorbitol, 5 mM betain, 100 µg/ml ampicillin until reaching an OD at 600 nm comprised between 0.8 and 1. Isopropyl-β-D-thiogalactopyranoside (IPTG) was then added to a final concentration of 1 mM and protein expression was continued at 20° C. overnight (approximately 16 h). The cells were collected by centrifugation at 4° C., 10,000 rpm for 20 min and the pellets were frozen at −80° C.

Cell Lysis

The pellets from 12 ml of culture cells were thawed on ice and resuspended in 1 ml of 50 mM Tris/HCl pH 7.4, containing 20 mM KCl, 0.5 mM DTT, 5 mM $MgCl_2$. One microliter of lysonase (Novagen) was added. Cells were incubated for 10 minutes at room temperature and then returned to ice for 20 minutes. Cell lysis was completed by sonication for 15 seconds. The bacterial extracts were then clarified by centrifugation at 4° C., 10,000 rpm for 20 min.

Enzymatic Reactions

The desired enzymatic reaction (conversion of mevalonate into isoprenol) was tested as follows.

The reaction medium contained 100 mM mevalonate, 40 mM ATP, 10 mM $MgCl_2$, 20 mM KCl, 0.5 mM DTT and enzyme preparation varying from 0.01 to 0.05 mg/ml of protein. 50 mM sodium citrate was used in the range of pH from 4 to 6, and 50 mM Tris-HCl for pH 7 and 7.5. Enzyme-free control assays were carried out in parallel. After 72 h incubation, inorganic phosphate was quantified colorimetrically according to the ammonium molybdate method (Gawronski J D, Benson D R, Anal. Biochem. 327 (2004) 114-118). A 50 µl sample (containing not more than 0.5 µmole of phosphate) was mixed with 150 µl of ammonium molybdate reagent containing 50% v/v acetone, 1.25 N $H_2SO_4$, 2.5 mM $(NH_4)_6Mo_7O_{24}$ and then with 10 µl 1 M citric acid. The mixture was incubated for 2 minutes at room temperature. The absorbance of ammonium phosphomolybdate formed was measured at 355 nm and the quantity of inorganic phosphate estimated using a calibration curve obtained with potassium phosphate.

The results are shown in FIG. 3.

During the initial screening, only assays using the recombinant strain expressing the genetic construct inferred from *Picrophilus torridus* MDP decarboxylase sequence gave rise to a reproducible increase in phosphate production over the background level.

EXAMPLE 2

Optimisation of *P. torridus* MDP Decarboxylase Expression in *E. coli*

The initial level of enzyme expression in *E. coli* BL21 was low, as judged from the faint band visible on SDS-PAGE gels. The Codon Optimization Index (CAI) of the native sequence for expression in *E. coli* measured with the "Optimizer" program available at http://genomes.urv.es/OPTIMIZER/, as based on the method of Sharp and Li (Nucl. Acids Res. 15 (1987), 1281-1295) gave a value as low as 0.23.

A gene sequence coding for an identical protein but containing codons better adapted for expression in *E. coli* was generated. It featured a CAI of 0.77.

The native sequence and the optimized sequence are shown in SEQ ID NO: 20 (native sequence of *P. torridus* (AAT43941) MDP decarboxylase including the His-tag) and SEQ ID NO: 21 (optimized sequence of *P. torridus* (AAT43941) MDP decarboxylase including the His-tag). The optimized sequence was synthesized by oligonucleotide concatenation and cloned in a pET25b expression vector. After transformation of *E. coli* strain BL21(DE3) and induction, the proteins were produced and analyzed on a gel as described according to the protocol described in Example 1. The same protocol was carried out with the native sequence for comparison.

Figure 4A:
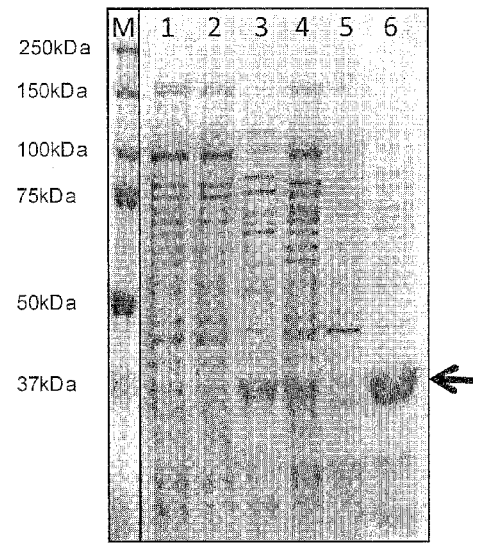

Expression levels using either the native nucleotide sequence or the sequence optimized for expression in *E. coli* were compared. The results in FIG. 4a show that the protein (arrow) corresponding to the optimized gene was clearly visible on the gel in the non-purified cell lysate (lane 4), which indicates a very notable increase in expression.

Figure 4B:
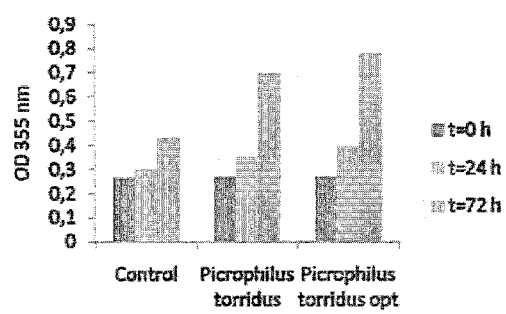

The expression of the protein was improved such that the crude lysate obtained with the optimized sequence contained a higher enzyme activity with mevalonate as substrate, as shown in FIG. 4b.

EXAMPLE 3

Characterization of the Reaction using the Optimized P. torridus MDPdecarboxylase The recombinant enzyme was purified as follows:

Protein Purification and Concentration

The pellets from 150 ml of culture cells were thawed on ice and resuspended in 5 ml of $Na_2HPO_4$ pH 8 containing 300 mM NaCl, 5 mM $MgCl_2$ and 1 mM DTT. Twenty microliters of lysonase (Novagen) was added. Cells were incubated 10 minutes at room temperature and then returned to ice for 20 minutes. Cell lysis was completed by sonication for 3×15 seconds. The bacterial extracts were then clarified by centrifugation at 4° C., 10,000 rpm for 20 min. The clarified bacterial lysates were loaded on PROTINO-1000 Ni-IDA column (Macherey-Nagel) allowing adsorption of 6-His tagged proteins ("6-His" disclosed as SEQ ID NO: 22). Columns were washed and the enzymes of interest were eluted with 4 ml of 50 mM $Na_2HPO_4$ pH 8 containing 300 mM NaCl, 5 mM $MgCl_2$, 1 mM DTT, 250 mM imidazole. Eluates were then concentrated and desalted on Amicon Ultra-4 10 kDa filter unit (Millipore) and resuspended in 250 µl 50 mM Tris-HCl pH 7.4 containing 0.5 mM DTT and 5 mM $MgCl_2$. Protein concentrations were quantified according to the Bradford method.

The purity of proteins thus purified was estimated as approximately 90%.

The activity of the enzyme was confirmed and further analyzed using a range substrate: The conversion rate was shown to increase with the concentration of mevalonate (FIG. 6).

EXAMPLE 4

Optimization of Reaction Conditions by Using a Cofactor

The same reaction as that described in Example 1 is carried out using purified preparations of optimized P. torridus MDP decarboxylase. In one of the samples, the phosphono-phosphate or phosphonamido-phosphate (FIG. 7) is added as cofactor at the concentration of 100 mM.

The conversion of mevalonate is observed using the colorimetric assay described in Example 1. It is found that when a cofactor is present, the amount of ATP consumed over time is markedly higher.

EXAMPLE 5

Screening of a Library of MDP Decarboxylase Homologs from the P. torridus Phylum Sequence of MDP decarboxylase enzymes inferred from the genomes of Thermoplasma volcanium (accession number Q97BY2) and Thermoplasma acidophilum (accession number Q9HIN1) were generated as in Example 1. Proteins were purified as described in Example 3 and assayed using the assay described in Example 1. A significant increase in phosphate production was observed from these vials, indicating that these enzymes were also active toward mevalonate. Results are shown in FIG. 5.

EXAMPLE 6

Method for Synthesizing Isoprenol from Glucose

E. coli K12 is transformed with an expression plasmid, carrying the genes of thiolase, HMG-CoA synthase and HMG-CoA reductase from Saccharomyces cerevisiae in order to overproduce mevalonate.

The strain is further transformed with a second, compatible expression plasmid carrying the optimized gene encoding the His-tagged version of MDP decarboxylase from Picrophilus torridus.

The resulting recombinant bacteria are then incubated in a fermenter in a mineral nutrient medium containing glucose, in the presence of oxygen and under moderate stirring. A significant production of isoprenol is measured using TLC or GC/MS analysis as follows:

TLC Analysis

For TLC analysis an aliquot of reaction medium is spotted on a silica-coated plate and chromatographed using as eluant ethyl acetate/heptane 1/1 v/v. Mevalonate, isoprenol, ATP. ADP are used as internal standards. After drying, plates are sprayed with alkaline KMnO4 reagent. $R_f$ for isoprenol is found to be 0.57.

GC/MS Analysis

An aliquot of 10 µl of reaction medium is centrifuged and the supernatant is transferred to a clean vial for isoprenol detection by GC/MS. 1 µL sample is separated by GC using a DB-5 column and the presence of isoprenol is monitored by mass spectrometry.

EXAMPLE 7

Measurement of Mevalonate Decarboxylase Activity and 3-Methyl-3-Buten-1-Ol (Isoprenol) Production Mevalonate is prepared from mevanolactone (Sigma) by hydrolysis with NaOH according to Campos et al. (Biochem. J. 2001. 353, 59-67).

The complete assay for mevalonate decarboxylation contains reaction buffer. 100 mM mevalonate, 40 mM ATP, 10 mM $MgCl_2$, 20 mM KCl, 0.5 mM DTT and enzyme preparation at a concentration ranging from 0.01 to 0.05 mg/ml of protein. 50 mM sodium citrate is used in the range of pH from 4 to 6, and 50 mM Tris-HCl for pH 7 and 7.5. Control reactions are carried out in the absence of enzyme, substrate or co-factor.

The progress of isoprenol production is followed by analyzing aliquots taken at successive time intervals from a reaction mixture incubated at 37° C. by thin-layer chromatography (TLC), gas chromatography/mass spectrometry (GC/MS) and product determination by permanganate assay. In parallel, the release of inorganic phosphate is quantified by ammonium molybdate method.

Permanganate Assay

The formation of products containing double-bonds is followed by oxidization with alkaline potassium permanganate solution, resulting in increase of absorbance at 420 nm.

To an aliquot of reaction mixture diluted with $H_2O$ to 120 μl, 80 μl of permanganate reagent, containing 5 mM $KMnO_4$ and 50 mM NaOH, is added. The mixture is kept at room temperature for 20 min and the absorbance at 420 nm is measured. The calibration curve is prepared using commercial isoprenol.

Inorganic Phosphate Quantification

Inorganic phosphate concentration is measured by spectroscopic colorimetry according to the ammonium molybdate method (Gawronski J D, Benson D R, Anal. Biochem. 327 (2004) 114-118). A 50 μl aliquot from the reaction assay (containing not more than 0.5 μmole of phosphate) is mixed with 150 μl ammonium molybdate reagent, containing 50% volume acetone, 1.25 N $H_2SO_4$, 2.5 mM $(NH_4)_6Mo_7O_{24}$ and then with 10 μl 1 M citric acid. The mixture is then incubated for 2 minutes at room temperature. The absorbance of ammonium phosphomolybdate formed was measured at 355 nm and the quantity of inorganic phosphate estimated using a calibration curve obtained with potassium phosphate.

The invention claimed is:

1. A method for the conversion of mevalonate to isoprenol, isoprene or isoamyl alcohol in vitro, comprising:
 (a) producing isoprenol in vitro by the step consisting essentially of incubating mevalonate with diphosphomevalonate decarboxylase and NTP, rNTP, dNTP or pyrophosphate, thereby producing isoprenol, and
 (b) isolating the isoprenol or further converting the isoprenol to isoprene or isoamyl alcohol,
 wherein the diphosphomevalonate decarboxylase comprises an amino acid sequence selected from the group consisting of SEQ ID NOs: 6, 7, 14 and 16.

2. The method of claim 1 wherein the enzyme comprises the amino acid sequence of SEQ ID NO: 6 or 16.

3. The method of claim 1 wherein one mole of NTP, rNTP, dNTP or pyrophosphate are consumed per mole of isoprenol produced.

4. The method of claim 1, wherein the isoprenol is converted to isoprene.

5. The method of claim 1, wherein the isoprenol is converted to isoamyl alcohol.

6. A method for producing isoprenol from mevalonate in an isolated cell,
 wherein the cell is a recombinant organism expressing a heterologous diphosphomevalonate decarboxylase and lacking mevalonate kinase activity, wherein the diphosphomevalonate decarboxylase comprises an amino acid sequence selected from the group consisting of SEQ ID NOs: 6, 7, 14 and 16,
 the method consisting essentially of
 (a) providing mevalonate or providing a carbon source to the cell under conditions in which mevalonate is produced; and (b) incubating the cell, thereby converting the mevalonate to isoprenol.

7. The method of claim 6, wherein the organism is a fungus.

8. The method of claim 6, wherein the heterologous diphosphomevalonate decarboxylase is from *Picrophilus torridus*.

9. The method of claim 6, wherein the cell is produced by transforming a unicellular organism with DNA encoding diphosphomevalonate decarboxylase.

10. A method for the production of isoprenol in a cell that does not naturally possess a mevalonate pathway consisting essentially of:
 (a) transforming the cell with genes encoding thiolase, HMG-CoA synthase, HMG-CoA reductase and diphosphomevalonate decarboxylase to obtain a recombinant cell;
 (b) incubating the transformed cell in the presence of a carbon source under conditions at which the cell produces mevalonate;
 (c) thereby producing isoprenol.

11. The method of claim 10, wherein the cell is *E. coli*.

* * * * *